United States Patent
Yoshida

(10) Patent No.: US 11,754,856 B2
(45) Date of Patent: Sep. 12, 2023

(54) METHOD FOR DESIGNING EYEGLASS LENS, METHOD FOR MANUFACTURING EYEGLASS LENS, EYEGLASS LENS, EYEGLASS LENS ORDERING DEVICE, EYEGLASS LENS ORDER RECEIVING DEVICE, AND EYEGLASS LENS ORDERING AND ORDER RECEIVING SYSTEM

(71) Applicant: NIKON-ESSILOR CO., LTD., Tokyo (JP)

(72) Inventor: Yoshinori Yoshida, Kawasaki (JP)

(73) Assignee: NIKON-ESSILOR CO., LTD., Tokyo (JP)

( * ) Notice: Subject to any disclaimer, the term of this patent is extended or adjusted under 35 U.S.C. 154(b) by 202 days.

(21) Appl. No.: 16/727,242

(22) Filed: Dec. 26, 2019

(65) Prior Publication Data

US 2020/0133022 A1    Apr. 30, 2020

Related U.S. Application Data

(63) Continuation of application No. PCT/JP2018/022631, filed on Jun. 13, 2018.

(30) Foreign Application Priority Data

Jul. 3, 2017  (JP) ................... 2017-130302

(51) Int. Cl.
*G02C 7/02*        (2006.01)
*A61B 3/00*        (2006.01)
(Continued)

(52) U.S. Cl.
CPC ............ *G02C 7/027* (2013.01); *A61B 3/0058* (2013.01); *A61B 3/032* (2013.01); *G02C 7/061* (2013.01); *G06Q 30/0633* (2013.01)

(58) Field of Classification Search
CPC ........ G02C 7/027; G02C 7/024; G02C 7/061; G02C 7/101; G02C 2202/10;
(Continued)

(56) References Cited

U.S. PATENT DOCUMENTS 8,082,188 B2   12/2011   Shinohara et al.
8,201,940 B2    6/2012   Suzuki
(Continued)

FOREIGN PATENT DOCUMENTS

CN     1340166 A    3/2002
CN     104284622 A  1/2015
(Continued)

OTHER PUBLICATIONS

Extended European Search Report dated Feb. 18, 2021, in corresponding European Patent Application No. 18828974.8.
(Continued)

*Primary Examiner* — Mustak Choudhury
(74) *Attorney, Agent, or Firm* — STAAS & HALSEY LLP

(57) ABSTRACT

A method for designing an eyeglass lens includes: displaying an image upon a display device while maintaining a positional relationship of a face of a subject and the display device; acquiring information in which visual sensitivity of the subject is evaluated on the basis of an impression received by the subject who has viewed the image; and designing an eyeglass lens on the basis of the information in which the sensitivity is evaluated.

31 Claims, 28 Drawing Sheets

(51) Int. Cl.
    *A61B 3/032*     (2006.01)
    *G02C 7/06*     (2006.01)
    *G06Q 30/0601*     (2023.01)

(58) Field of Classification Search
    CPC ......... A61B 3/0033; A61B 3/02; A61B 3/022;
              A61B 3/06; A61B 3/032; A61B 3/0058
    See application file for complete search history.

(56) References Cited

U.S. PATENT DOCUMENTS

| | | | |
|---|---|---|---|
| 8,690,323 | B2 | 4/2014 | Hatanaka |
| 2004/0032565 | A1 | 2/2004 | Yamakaji et al. |
| 2010/0283963 | A1* | 11/2010 | Giraudet ............... G02C 7/065 351/159.42 |
| 2010/0296055 | A1 | 11/2010 | Esser et al. |
| 2010/0309428 | A1* | 12/2010 | Altheimer ............. G02C 7/027 703/2 |
| 2012/0105609 | A1 | 5/2012 | Qi |
| 2012/0106813 | A1* | 5/2012 | Drobe .................. A61B 5/7475 382/128 |
| 2014/0168607 | A1* | 6/2014 | Qi ........................ A61B 3/0058 351/159.75 |
| 2015/0163480 | A1 | 6/2015 | Qi et al. |
| 2015/0371415 | A1 | 12/2015 | Qi |
| 2016/0235291 | A1* | 8/2016 | Goh ..................... A61B 3/0091 |
| 2016/0327808 | A1* | 11/2016 | Hatanaka ............... G02C 7/066 |
| 2017/0052389 | A1 | 2/2017 | Hatanaka |
| 2017/0299888 | A1 | 10/2017 | Tranvouez et al. |
| 2017/0371179 | A1* | 12/2017 | Scherlen ................ G02C 7/027 |
| 2018/0140178 | A1* | 5/2018 | Anderson ............... A63F 13/85 |

FOREIGN PATENT DOCUMENTS

| | | |
|---|---|---|
| CN | 105009124 A | 10/2015 |
| EP | 1 862 110 A1 | 12/2007 |
| EP | 2 886 040 A1 | 6/2015 |
| EP | 3 006 991 A1 | 4/2016 |
| JP | 11-119172 | 4/1999 |
| JP | 4306702 | 5/2009 |
| JP | 2010-517088 | 5/2010 |
| JP | 2011-48327 | 3/2011 |
| JP | 2011-107239 | 6/2011 |
| JP | 2012-95694 | 5/2012 |
| JP | 5094968 | 9/2012 |
| JP | 2017-90729 | 5/2017 |
| WO | WO 2013/175923 A1 | 11/2013 |
| WO | WO 2014/122834 A1 | 8/2014 |
| WO | WO 2015/125848 A1 | 8/2015 |
| WO | WO 2016/055265 A1 | 4/2016 |

OTHER PUBLICATIONS

Chinese Office Action dated Jul. 10, 2020, in corresponding Chinese Patent Application No. 201880044839.1.
International Search Report dated Sep. 18, 2018 in corresponding International Patent Application No. PCT/JP2018/022631.
Office Action, dated Sep. 27, 2022, in Japanese Patent Application No. 2019-527603 (7 pp.).
Office Action, dated Apr. 22, 2022, in Chinese Patent Application No. 202110162461.9 (18 pp.).
Office Action, dated Apr. 26, 2022, in Japanese Patent Application No. 2019-527603 (9 pp.).
Office Action, dated Dec. 20, 2022, in corresponding Japanese Patent Application No. 2019-527603 (8 pp.).

* cited by examiner

FIG.4A
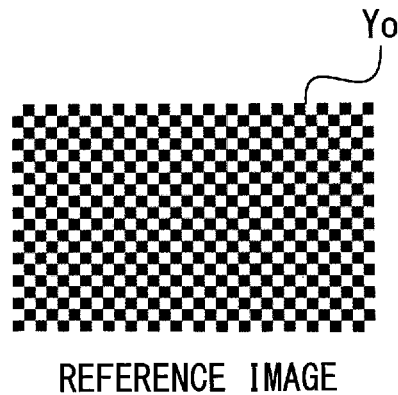
REFERENCE IMAGE
FIG.4B   DISTORTION DIRECTION:90°
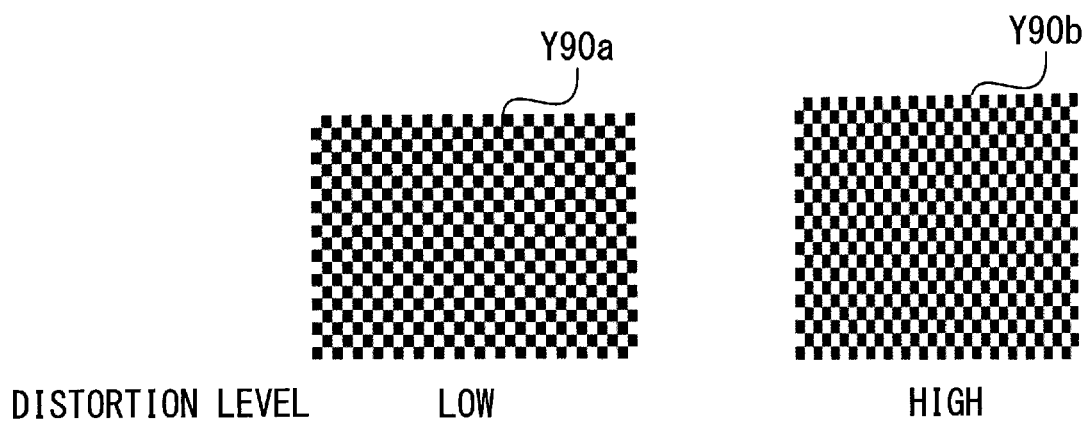
DISTORTION LEVEL          LOW                                    HIGH
FIG.4C   DISTORTION DIRECTION:0°
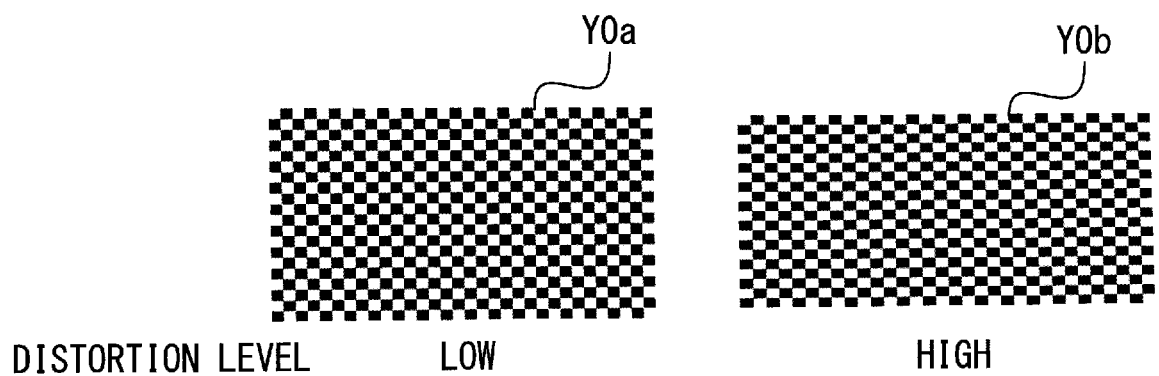
DISTORTION LEVEL          LOW                                    HIGH FIG.5A
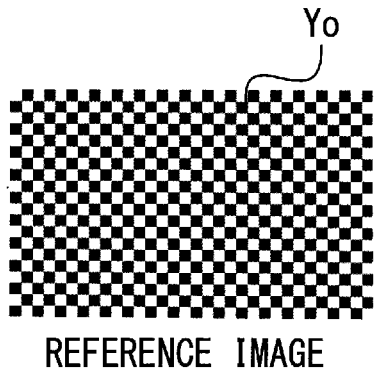
REFERENCE IMAGE
FIG.5B  DISTORTION DIRECTION: 45°
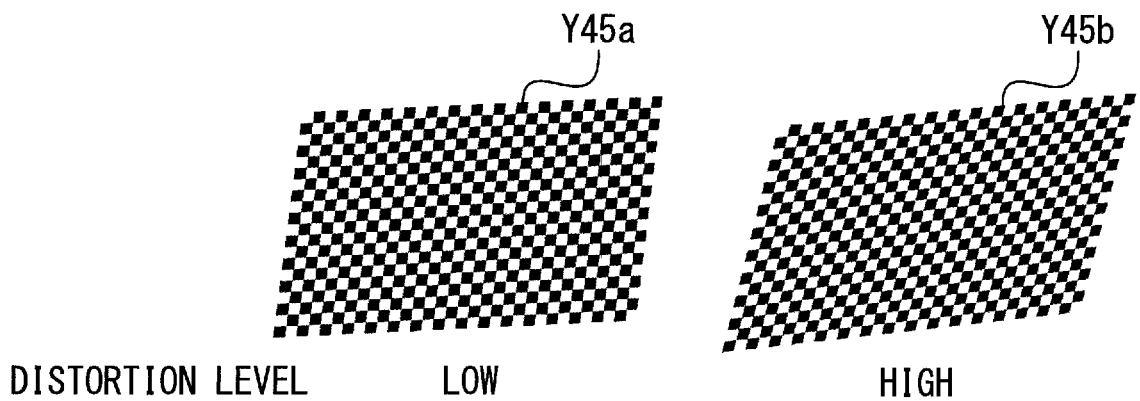
DISTORTION LEVEL            LOW                      HIGH
FIG.5C  DISTORTION DIRECTION: 135°
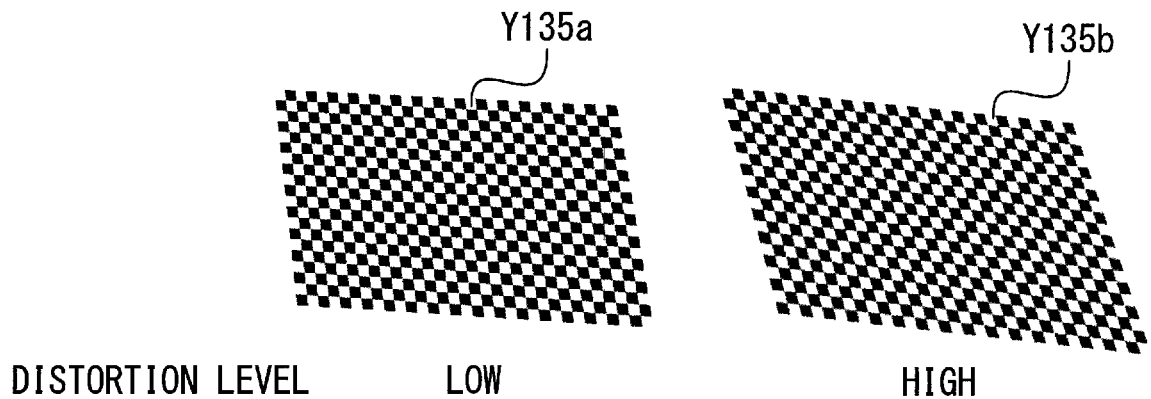
DISTORTION LEVEL            LOW                      HIGH

[LENS INFORMATION] — 101

| | PRODUCT NAME | S POWER | C POWER | AXIS ANGLE | ADDITION |
|---|---|---|---|---|---|
| RIGHT | LENS A | -2.25 | -0.25 | 90 | 2.00 |
| LEFT | LENS A | -2.25 | -0.25 | 90 | 2.00 |

[PROCESSING SPECIFICATION INFORMATION] — 102

| | PROCESSING SPECIFICATION |
|---|---|
| RIGHT | EXTERNAL DIAMETER 60 |
| LEFT | EXTERNAL DIAMETER 60 |

[TINTING INFORMATION] — 103

| | TINTING COLOR | TINTING METHOD | DENSITY |
|---|---|---|---|
| | COLOR A | HALF | 15% |

[FITTING POINT INFORMATION] — 104

| | PD | FP |
|---|---|---|
| RIGHT | 32.5 | 2 |
| LEFT | 32.5 | 2 |

[SENSITIVITY INFORMATION] — 106a

| | INTENSITY OF SENSITIVITY TO DISTORTION |
|---|---|
| 0° | 4 |
| 45° | 5 |
| 90° | 4 |
| 135° | 2 |

[FRAME INFORMATION] — 105

| MODEL NAME | FRAME CLASSIFICATION | FRAME PD |
|---|---|---|
| MODEL 1 | | |

FIG.19

[LENS INFORMATION] 101

| | PRODUCT NAME | S POWER | C POWER | AXIS ANGLE | ADDITION |
|---|---|---|---|---|---|
| RIGHT | LENS A | -2.25 | -0.25 | 90 | 2.00 |
| LEFT | LENS A | -2.25 | -0.25 | 90 | 2.00 |

[PROCESSING SPECIFICATION INFORMATION] 102

| | PROCESSING SPECIFICATION |
|---|---|
| RIGHT | EXTERNAL DIAMETER 60 |
| LEFT | EXTERNAL DIAMETER 60 |

[TINTING INFORMATION] 103

| | TINTING COLOR | TINTING METHOD | DENSITY |
|---|---|---|---|
| | COLOR A | HALF | 15% |

[FITTING POINT INFORMATION] 104

| | PD | FP |
|---|---|---|
| RIGHT | 32.5 | 2 |
| LEFT | 32.5 | 2 |

[SENSITIVITY INFORMATION] 106b

| | INTENSITY OF SENSITIVITY TO RANGE OF BLURRING |
|---|---|
| DISTANCE AREA | 3 |
| INTERMEDIATE AREA | 2 |
| NEAR AREA | 3 |

[FRAME INFORMATION] 105

| MODEL NAME | FRAME CLASSIFICATION | FRAME PD |
|---|---|---|
| MODEL 1 | | |

100b

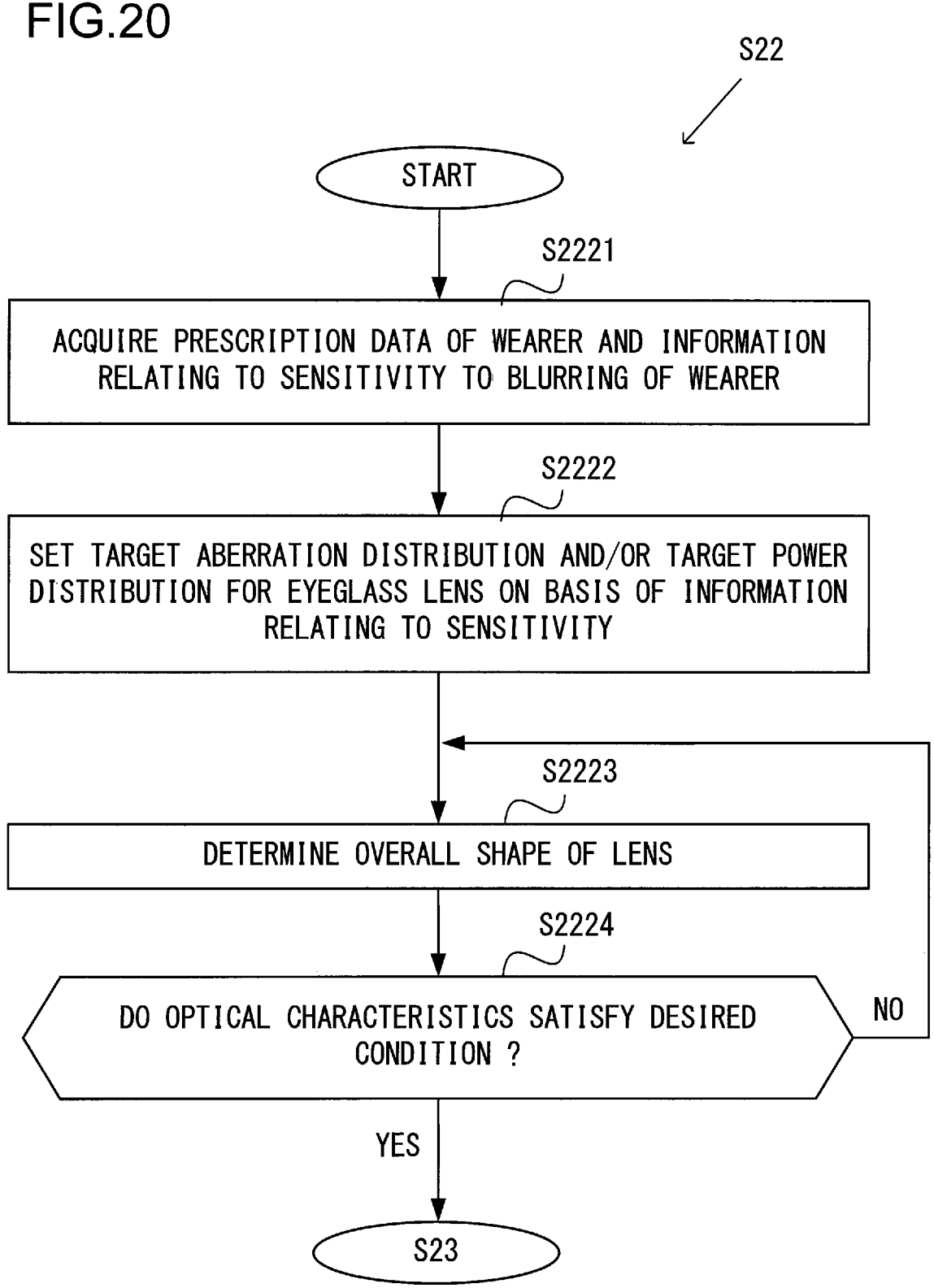

FIG.24A P1
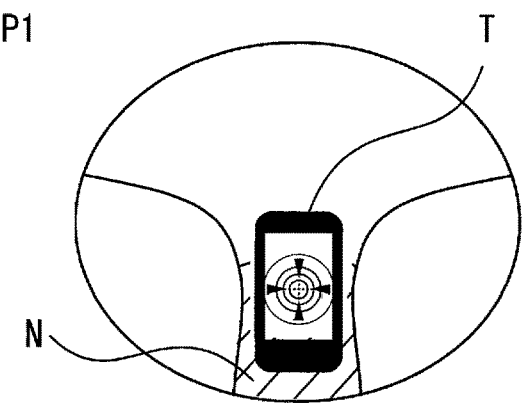
FIG.24B P2
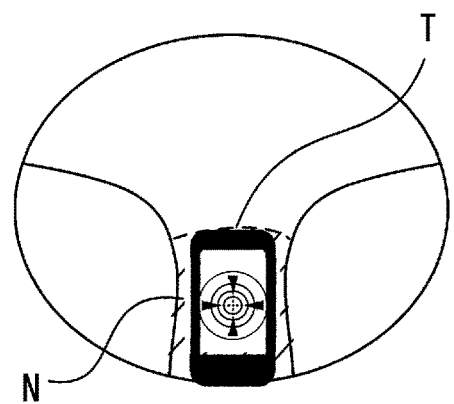
FIG.24C P3
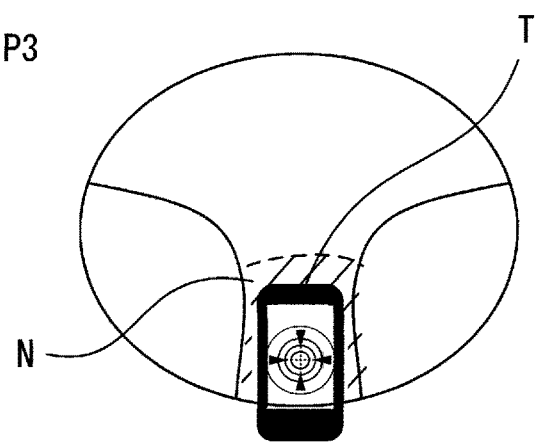
FIG.24D P4
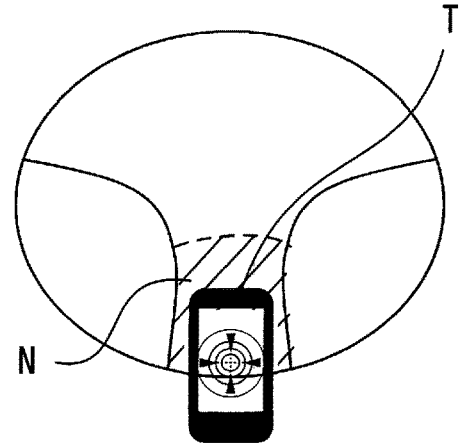

[LENS INFORMATION] — 101

| | PRODUCT NAME | S POWER | C POWER | AXIS ANGLE | ADDITION |
|---|---|---|---|---|---|
| RIGHT | LENS A | -2.25 | -0.25 | 90 | 2.00 |
| LEFT | LENS A | -2.25 | -0.25 | 90 | 2.00 |

[PROCESSING SPECIFICATION INFORMATION] — 102

| | PROCESSING SPECIFICATION |
|---|---|
| RIGHT | EXTERNAL DIAMETER 60 |
| LEFT | EXTERNAL DIAMETER 60 |

[TINTING INFORMATION] — 103

| TINTING COLOR | TINTING METHOD | DENSITY |
|---|---|---|
| COLOR A | HALF | 15% |

[FITTING POINT INFORMATION] — 104

| | PD | FP |
|---|---|---|
| RIGHT | 32.5 | 2 |
| LEFT | 32.5 | 2 |

[SENSITIVITY INFORMATION] — 106c

| | INTENSITY OF SENSITIVITY TO HEIGHT OF LINE OF SIGHT |
|---|---|
| NEAR AREA | 2 |
| INTERMEDIATE AREA | 3 |

[FRAME INFORMATION] — 105

| MODEL NAME | FRAME CLASSIFICATION | FRAME PD |
|---|---|---|
| MODEL 1 | | |

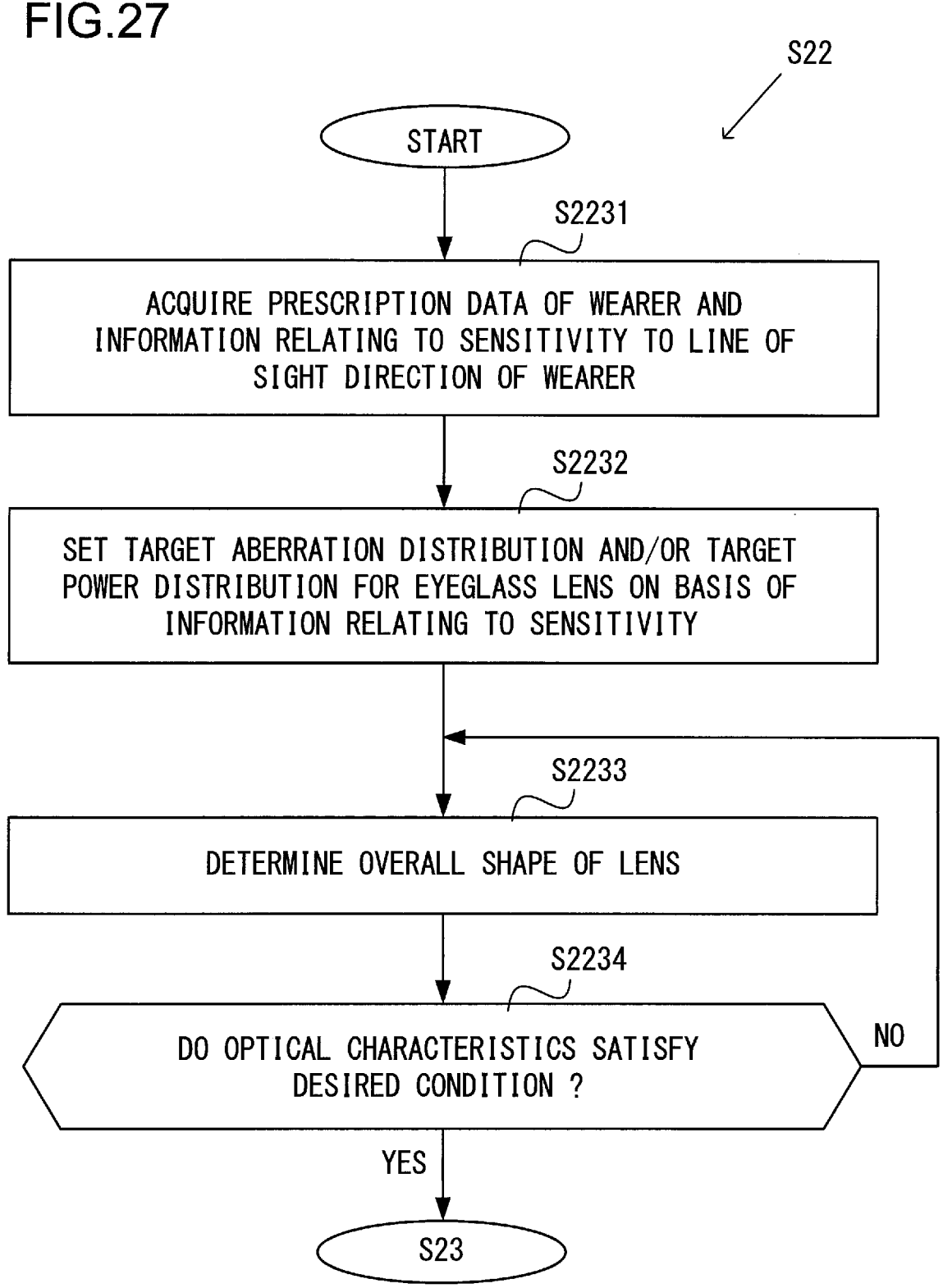

METHOD FOR DESIGNING EYEGLASS LENS, METHOD FOR MANUFACTURING EYEGLASS LENS, EYEGLASS LENS, EYEGLASS LENS ORDERING DEVICE, EYEGLASS LENS ORDER RECEIVING DEVICE, AND EYEGLASS LENS ORDERING AND ORDER RECEIVING SYSTEM

CROSS-REFERENCE TO RELATED APPLICATIONS

This application is a continuation of International Application No. PCT/JP2018/022631 filed Jun. 13, 2018, which claims priority benefit to Japanese Patent Application No. 2017-130302, filed Jul. 3, 2017, the disclosures of which are hereby incorporated in their entirety by reference.

TECHNICAL FIELD

The present invention relates to a method for designing an eyeglass lens, a method for manufacturing an eyeglass lens, an eyeglass lens, an eyeglass lens ordering device, an eyeglass lens order receiving device and an eyeglass lens ordering and order receiving system.

BACKGROUND ART

Various design methods have been proposed for producing eyeglass lenses that match the characteristics of individual wearers. For example, an eyeglass lens ordering and order receiving system that employs a synthetic image for showing what vision would be like when an eyeglass lens is worn is described in PTL1.

CITATION LIST

Patent Literature

PTL1: Japanese Patent 4,306,702.

SUMMARY OF INVENTION

Solution to Problem

According to the 1st aspect of the present invention, a method for designing an eyeglass lens comprises: displaying an image upon a display device while maintaining a positional relationship of a face of a subject and the display device; acquiring information in which visual sensitivity of the subject is evaluated on the basis of an impression received by the subject who has viewed the image; and designing an eyeglass lens on the basis of the information in which the sensitivity is evaluated.

According to the 2nd aspect of the present invention, in the method for designing an eyeglass lens according to the 1st aspect, it is preferred that the display device is disposed at a position based upon a height of an eye of the subject.

According to the 3rd aspect of the present invention, in the method for designing an eyeglass lens according to the 1st or 2nd aspect, in the display of the image, a plurality of images are displayed, each having different distortion; and in the evaluation of the sensitivity, the sensitivity of the subject to distortion is evaluated on the basis of the impressions received by the subject who has viewed the plurality of images.

According to the 4th aspect of the present invention, in the method for designing an eyeglass lens according to the 3rd aspect, the plurality of images differ by at least one of distortion level of the distortion and distortion direction of the distortion.

According to the 5th aspect of the present invention, in the method for designing an eyeglass lens according to the 3rd or 4th aspect, each of the images is distorted in one or a plurality of partial regions, or in all regions.

According to the 6th aspect of the present invention, in the method for designing an eyeglass lens according to the 5th aspect, in each of the plurality of partial regions, the images are mutually different with regard to at least one of the distortion level and the distortion direction.

According to the 7th aspect of the present invention, in the method for designing an eyeglass lens according to the 5th or 6th aspect, the image is distorted both in one partial region on one side from the center of the image, and in a partial region on the side opposite to the one side from the center of the image.

According to the 8th aspect of the present invention, in the method for designing an eyeglass lens according to the 1st or 2nd aspect, in the display of the image, a plurality of images are displayed, each having a different range of blurring; and in the evaluation of the sensitivity, the sensitivity of the subject to blurring is evaluated on the basis of the impressions received by the subject who has viewed the plurality of images.

According to the 9th aspect of the present invention, in the method for designing an eyeglass lens according to the 8th aspect, in the plurality of images, blurring levels of the blurring and/or regions of the blurring are different.

According to the 10th aspect of the present invention, in the method for designing an eyeglass lens according to the 8th or 9th aspect, each of the images comprises a plurality of regions whose blurring levels are mutually different, and/or blurring in which the blurring level changes continuously.

According to the 11th aspect of the present invention, in the method for designing an eyeglass lens according to any one of the 8th to 10th aspects, adjacent to the blurring, the images comprise a region in which the blurring level changes stepwise or continuously.

According to the 12th aspect of the present invention, in the method for designing an eyeglass lens according to any one of the 8th to 11th aspects, in the display of the image, a region in which the blurring level is relatively large is displayed so as to be disposed below a region in which the blurring level is relatively small or a region where there is no blurring; and in the evaluation of the sensitivity, the sensitivity to blurring when the subject is looking at an object at a long distance is evaluated.

According to the 13th aspect of the present invention, in the method for designing an eyeglass lens according to any one of the 8th to 11th aspects, in the display of the image, a region in which the blurring level is relatively large is displayed so as to be disposed above a region in which the blurring level is relatively small or a region where there is no blurring; and in the evaluation of the sensitivity, the sensitivity to blurring when the subject is looking at an object at a short distance is evaluated.

According to the 14th aspect of the present invention, in the method for designing an eyeglass lens according to any one of the 8th to 11th aspects, in the display of the image, a region in which the blurring level is relatively small or a region where there is no blurring is displayed so as to be disposed surrounded by a region in which the blurring level is relatively large; and in the evaluation of the sensitivity, the sensitivity to blurring when the subject is looking at an object at an intermediate distance is evaluated.

According to the 15th aspect of the present invention, in the method for designing an eyeglass lens according to the 1st or 2nd aspect, in the display of the image, a plurality of images whose positions in a portion of a field of view of the subject are different are displayed while changing over between them; and in the evaluation of the sensitivity, the sensitivity of the subject to a direction of a line of sight at a predetermined distance is evaluated on the basis of the impressions received by the subject who has viewed the plurality of images.

According to the 16th aspect of the present invention, in the method for designing an eyeglass lens according to 15th aspect, in the display of the image, a plurality of images are displayed at different heights; and the sensitivity of the subject to a height of a line of sight at the predetermined distance is evaluated on the basis of the impressions received by the subject who has viewed the plurality of images.

According to the 17th aspect of the present invention, in the method for designing an eyeglass lens according to the 15th to 16th aspect, the portion of the field of view corresponds to any one region selected from among a distance area of a progressive power lens, a near area thereof and an intermediate region thereof between the distant area and the near area; and the predetermined distance is a distance seen through the one region that has been selected.

According to the 18th aspect of the present invention, in the method for designing an eyeglass lens according to any one of the 15th to 17th aspects, in the display of the image, a calibration image is displayed for adjusting a positional relationship between a height of an eye of the subject and a position of the image.

According to the 19th aspect of the present invention, it is preferred that the method for designing an eyeglass lens according to any one of the 15th to 18th aspects further comprises: capturing a positional relationship image that includes the subject and an object, wherein: in the display of the image, an image of the object is displayed as the image at a position that is set on the basis of a positional relationship between the subject and the object, obtained from the positional relationship image.

According to the 20th aspect of the present invention, in the method for designing an eyeglass lens according to any one of the 15th to 19th aspects, in the evaluation of the sensitivity, the sensitivity of the subject to a direction of a line of sight at a short distance is evaluated on the basis of the impressions received by the subject who has viewed the images; and the images are images of at least one selected from a portable telephone, a book, and a newspaper.

According to the 21st aspect of the present invention, in the method for designing an eyeglass lens according to any one of the 15th to 19th aspects, in the evaluation of the sensitivity, the sensitivity of the subject to a direction of a line of sight at an intermediate distance is evaluated on the basis of the impressions received by the subject who has viewed the images; and the images are images of at least one selected from a personal computer, a tablet terminal, and a musical score.

According to the 22nd aspect of the present invention, in the method for designing an eyeglass lens according to any one of the 1st to 21st aspects, the images are processed images obtained by processing an image in which at least a portion of surroundings of the subject have been captured.

According to the 23rd aspect of the present invention, in the method for designing an eyeglass lens according to any one of the 1st to 22nd aspects, the images are processed images obtained by processing an image depicting a virtual space.

According to the 24th aspect of the present invention, in the method for designing an eyeglass lens according to any one of the 1st to 23rd aspects, movement detection of detecting movement of the subject; and image changing of changing the images on the basis of movement of the subject that has been detected.

According to the 25th aspect of the present invention, in the method for designing an eyeglass lens according to any one of the 1st to 24th aspects, detecting a direction of a line of sight of the subject who has viewed the image, wherein: in the evaluation of the sensitivity, the sensitivity of the subject is evaluated on the basis of the direction of the line of sight.

According to the 26th aspect of the present invention, in the method for designing an eyeglass lens according to any one of the 1st to 25th aspects, in the display of the image, a right eye image and a left eye image that are mutually different are displayed to the right eye and to the left eye of the subject, respectively.

According to the 27th aspect of the present invention, in the method for designing an eyeglass lens according to the 26th aspects, parallax is present between the right eye image and the left eye image for enabling stereoscopic vision.

According to the 28th aspect of the present invention, a method for manufacturing an eyeglass lens is a method in which an eyeglass lens is manufactured that has been designed according to a method for designing an eyeglass lens according to any one of the 1st to 27th aspects.

According to the 29th aspect of the present invention, an eyeglass lens has been manufactured according to the method for manufacturing an eyeglass lens according to the 28th aspect.

According to the 30th aspect of the present invention, an eyeglass lens ordering device comprises: an input unit that inputs information in which visual sensitivity of a subject is evaluated on the basis of an impression received by the subject who has viewed an image displayed while maintaining a positional relationship between a face of the subject and a display device; and a communication unit that transmits the information inputted via the input unit, or a design parameter calculated on the basis of the information, to an eyeglass lens order receiving device.

According to the 31th aspect of the present invention, an eyeglass lens order receiving device comprises: a reception unit that receives information relating to visual sensitivity of a subject, or a design parameter calculated on the basis of the information, the visual sensitivity being evaluated on the basis of an impression received by the subject who has viewed an image displayed while maintaining a positional relationship between a face of the subject and a display device; and a design unit that designs an eyeglass lens on the basis of the information or the design parameter.

According to the 32th aspect of the present invention, an eyeglass lens ordering and order receiving system comprises: the eyeglass lens ordering device according to the 30th aspect; and an eyeglass lens order receiving device comprising a reception unit that receives information relating to visual sensitivity of a subject, or a design parameter calculated on the basis of the information, the visual sensitivity being evaluated on the basis of an impression received by the subject who has viewed an image displayed while maintaining a positional relationship between a face of the subject and a display device and a design unit that designs an eyeglass lens on the basis of the information or the design parameter.

BRIEF DESCRIPTION OF DRAWINGS

FIG. 4A is a conceptual figure showing an original image with no distortion.

FIG. 4B is a conceptual figure showing distorted images in which the distortion direction is 90°.

FIG. 4C is a conceptual figure showing distorted images in which the distortion direction is 0°.

FIG. 5A is a conceptual figure showing an original image with no distortion.

FIG. 5B is a conceptual figure showing distorted images in which the distortion direction is 45°.

FIG. 5C is a conceptual figure showing distorted images in which the distortion direction is 135°.

FIG. 10 is a figure showing an example of an ordering screen.

FIG. 19 is a figure showing an example of an ordering screen.

FIG. 20 is a flow chart showing flow of a method for designing an eyeglass lens according to the embodiment.

FIG. 24A is a conceptual figure for explanation of ways in which a display image is displayed and shows a case in which the display image is displayed at a highest position.

FIG. 24B is a conceptual figure for explanation of ways in which a display image is displayed and shows a case in which the display image is displayed at a second highest position.

FIG. 24C is a conceptual figure for explanation of ways in which a display image is displayed and shows a case in which the display image is displayed at a third highest position.

FIG. 24D is a conceptual figure for explanation of ways in which a display image is displayed and shows a case in which the display image is displayed at a fourth highest position.

FIG. 26 is a figure showing another example of an ordering screen.

FIG. 27 is a flow chart showing flow of a method for designing an eyeglass lens according to the embodiment.

DESCRIPTION OF EMBODIMENTS

In the following embodiments, various methods for designing an eyeglass lens and so on will now be described with reference to drawings as appropriate. In the following explanation, when reference is made to "upper", "lower", "upper portion", "lower portion", "left side", "right side", and so on of the eyeglass lens, it will be supposed that these terms are based upon a positional relationship of the eyeglass lens as seen from a wearer when wearing that eyeglass lens.

The First Embodiment

In a method for an eyeglass lens according to the first embodiment, information is acquired in which sensitivity to visual distortion of a wearer of the eyeglass lens being designed is evaluated, and the eyeglass lens is designed on the basis of that information. In the following, testing for evaluating the sensitivity of the wearer to distortion will be termed "distortion sensitivity testing".

In the embodiments described below, "distortion" means that an object is recognized as an image having a shape that is different from its actual shape, and principally that the image of the object is stretched or shrunk in some direction, such as vertically, horizontally, slantingly, or the like. The term "distortion" includes distortion aberration, but, in the present embodiment, it is supposed principally to be stretching or shrinking of an image of an object that takes place due to the object being viewed through a surface where refractive power or astigmatism changes, such as a lens surface of a progressive power lens.

It should be understood that the method for designing an eyeglass lens according to the present embodiment can be widely applied when the object is recognized as an image having a shape that is different from its actual shape, such as distortion aberration or the like.

Figure 1A:
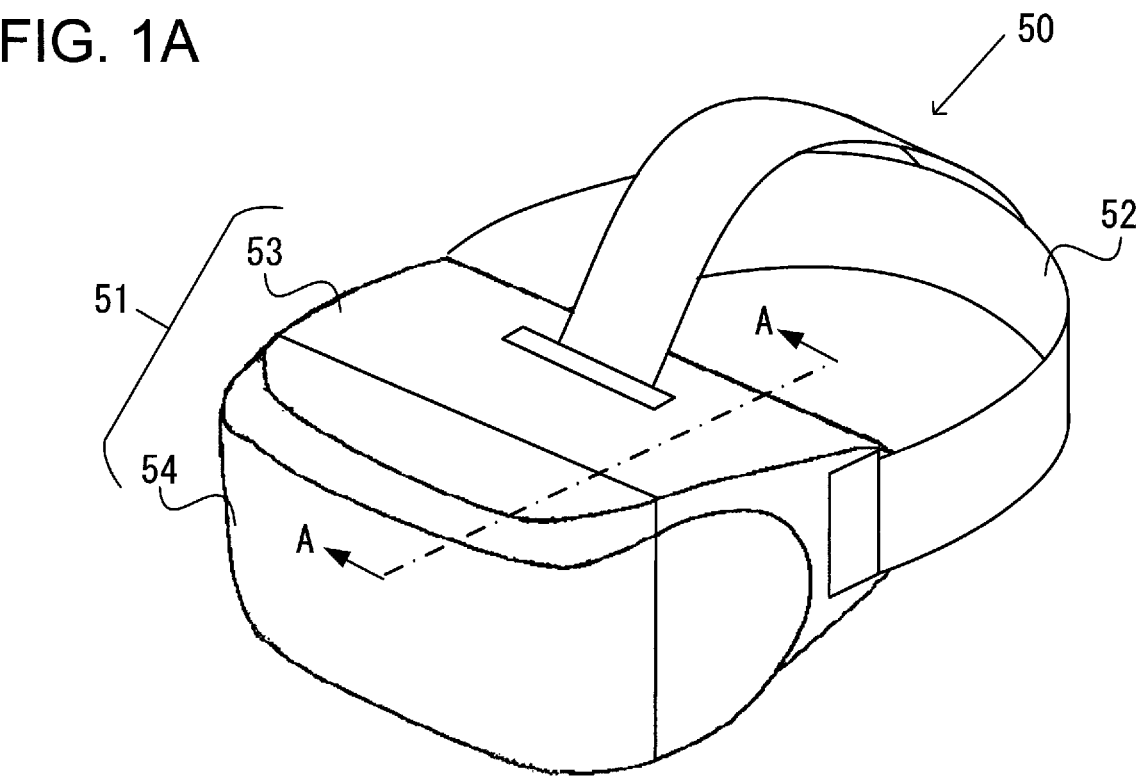
FIG. 1A is a perspective view showing external appearance of a display device related to a method for designing an eyeglass lens according to an embodiment.

FIG. 1A is a perspective view showing external appearance of a head mounted display (HMD) type display device 50 worn by a subject for distortion sensitivity testing in the method for designing an eyeglass lens according to the present embodiment. This display device 50 comprises a main body 51 that includes a display screen, and a support unit 52 that mounts the main body 51 to a head of the subject so that the positional relationship of a face of the subject and the display device 50 is maintained. The main body 51 comprises a lens holding unit 53 and a display screen holding unit 54 that is disposed upon a front surface of the lens holding unit 53.

Figure 1B:
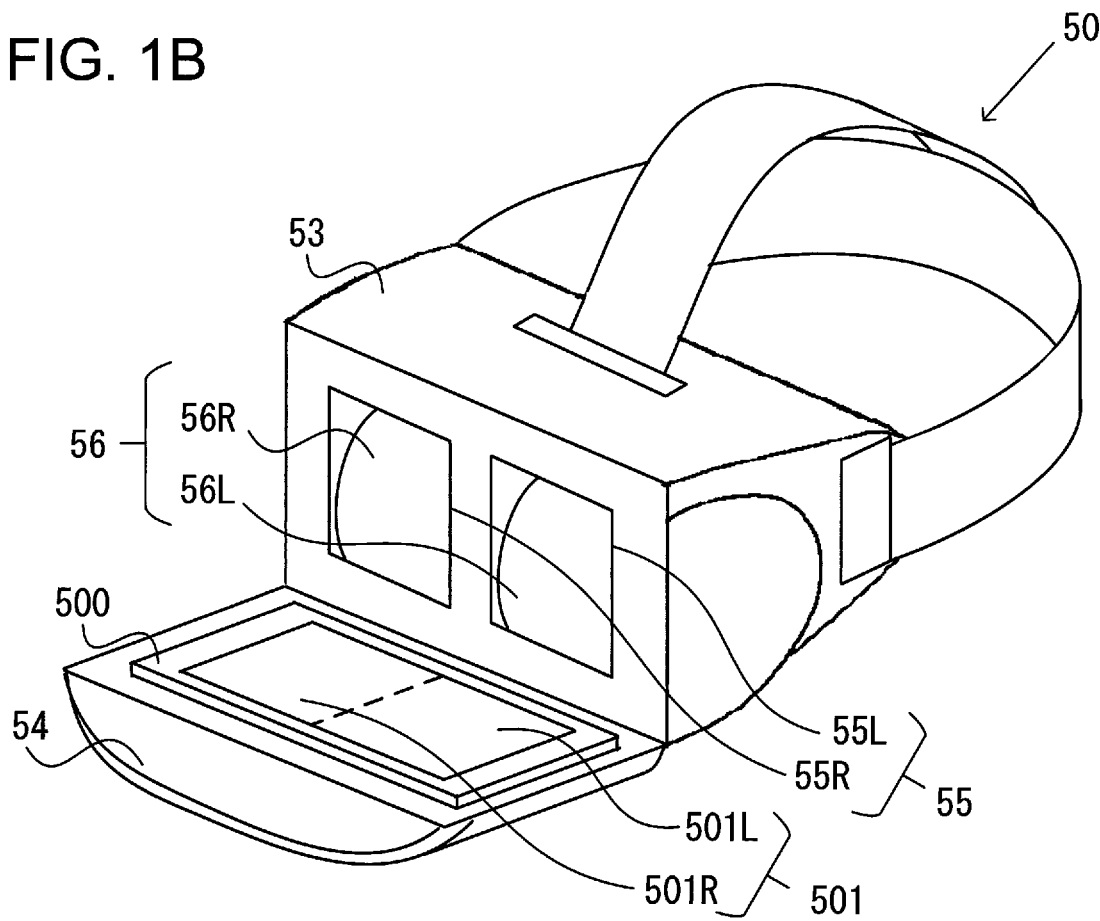
FIG. 1B is a perspective view showing an internal structure of the display device related to the method for designing an eyeglass lens according to the embodiment.

FIG. 1B is a perspective view showing an internal structure of the display device 50. The display screen holding unit 54 is coupled to the lens holding unit 53 via an opening and closing mechanism such as a hinge or the like, so that, by tilting the display screen holding unit 54 forward with respect to the lens holding unit 53, it is possible to check the internal structure, and to operate devices and so on that are disposed inside.

The lens holding unit 53 internally comprises opening portions 55L, 55R through which lines of sight from a left eye and a right eye of a subject who is viewing the display screen respectively pass, and image formation lenses 56L, 56R for forming images from light from the display screen in the left eye and in the right eye of the subject respectively.

These image formation lenses may each include one or a plurality of lenses. The display screen holding unit 54 comprises a portable type display device 500 that is detachably disposed thereto. In the following, this portable type display device 500 is explained as being a portable terminal 500 such as a smartphone or the like. It should be understood, however, that the display device 50 could also be of an integrated type in which a display screen is integrated into the main body 51. In such a case, functions possessed by the portable terminal 500 that will be described hereinafter are provided to the main body 51.

The portable terminal 500 includes a display screen 501. This display screen 501 displays a left eye image 501L to the left eye of the subject and a right eye image 501R to the right eye of the subject, respectively. In the case of the state of FIG. 1A in which the lens holding unit 53 and the display screen holding unit 54 are arranged to face one another, the left eye image 501L is displayed so as to face the opening portion 55L, while the right eye image 501R is displayed so as to face the opening portion 55R.

Figure 2:
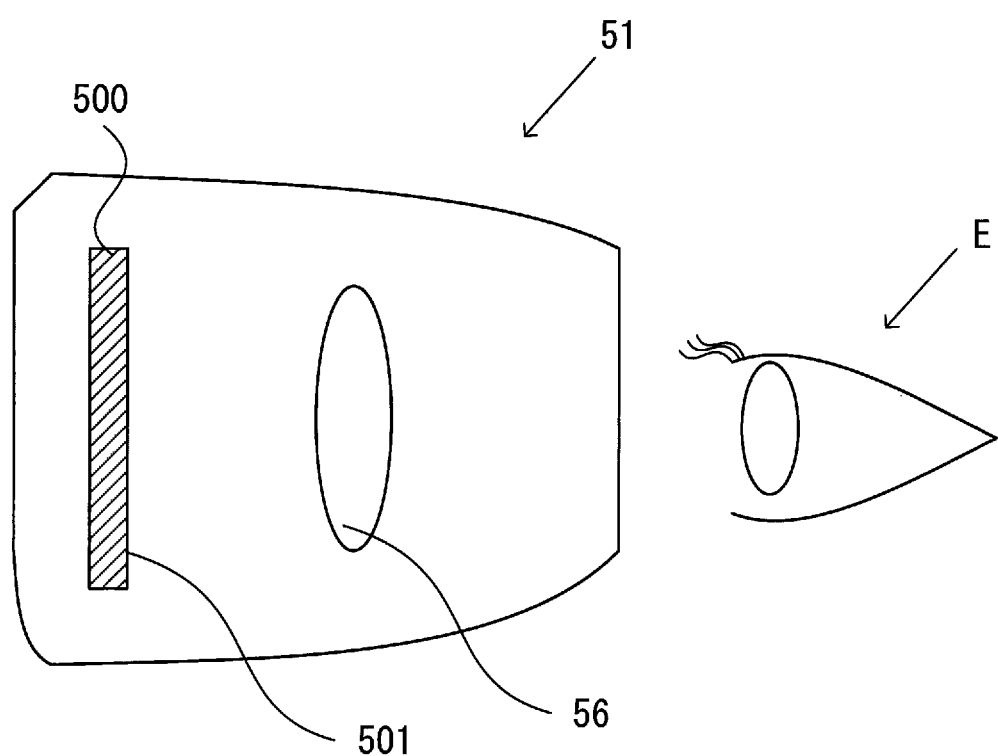
FIG. 2 is a sectional view, schematically showing the internal structure of the display device.

FIG. 2 is a figure schematically showing a cross section of the main body 51 of the display device 50 (A-A in FIG. 1A). The display device 50 is arranged on the basis of height of the eye E of the subject, so that the eye E of the subject opposes the image formation lens 56. Light emitted from the display screen 501 of the portable terminal 500 passes through the image formation lens 56, and enters into the eye E of the subject. The image formation lens 56 has a positive refractive power, and, due to this, it is possible for the subject easily to focus the eye E upon the display screen 501 provided in the HMD.

Figure 3:
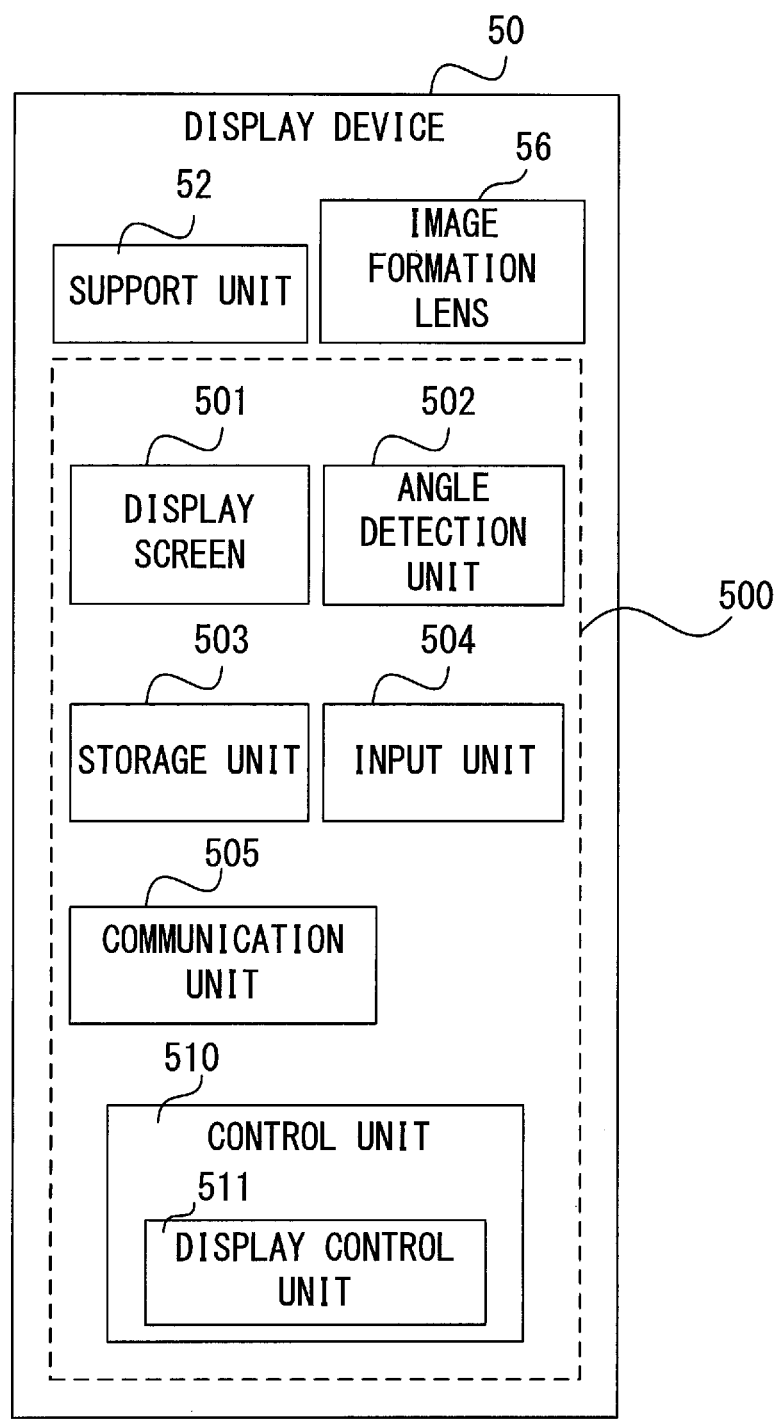
FIG. 3 is a conceptual figure, schematically showing various functions of the display device.

FIG. 3 is a conceptual figure, schematically showing various functions of respective portions of the display device 50. In the present embodiment, the portable terminal 500 possesses various functions in relation to image display other than the functions possessed by the support unit 52 and the image formation lens 56 and so on described above.

The mobile terminal 500 comprises the display screen 501, an angle detection unit 502, a storage unit 503, an input unit 504, a communication unit 505, and a control unit 510. And the control unit 510 comprises a display control unit 511.

The angle detection unit 502 comprises an acceleration sensor, a geomagnetism sensor, and/or a gyro sensor, and detects an orientation, an angle, and/or an angular velocity etc. of the portable terminal 500 and obtains values thereof. From these detected values the control unit 510, which will be described hereinafter, calculates an angle to which the subject has rotated his/her head and a direction in which the subject is facing. And the storage unit 503 is configured to include a non-volatile storage medium, and stores programs of various types such as an image display program that is employed in distortion sensitivity testing and so on, and display images and so on.

The input unit 504 is configured to include buttons, a touch panel that is integrated with the display screen 501, or the like, and receives operations of the portable terminal 500, such as input of parameters of various types employed in distortion sensitivity testing and so on. And the communication unit 505 is configured to include a communication device for performing wireless communication and performs acquisition of images and programs that are employed in distortion sensitivity testing, and, as appropriate, also performs transmission and reception of required information.

It should be understood that images to be employed in the distortion sensitivity testing may be obtained from the exterior by using a detachable storage medium.

The control unit 511 of the portable terminal 500 is configured to include a processor such as a CPU or the like, and executes a program stored in the storage unit 503, thus implementing each operation of the portable terminal 500. And the display control unit 511 displays distorted images that will be explained hereafter upon the display screen 501 according to a sequence or rules that are determined by a program for image display concerning distortion sensitivity testing.

FIGS. 4A, 4B and 4C are figures for explanation of images for distortion sensitivity testing that are displayed upon the display screen 501 and that include distortions (hereinafter these will be termed "distorted images Y"). In the following explanation, an original image Yo before creation of distorted images Y will be taken as being a rectangular image having a pattern consisting of black and white squares that are arranged alternatingly without two squares of the same color ever being adjacent to one another (i.e., arranged in a checkerboard pattern), as shown in FIG. 4A. And FIG. 4B and FIG. 4C show distorted images Y. It should be understood that, in the following embodiments, a distortion direction is defined as being a direction in which an original image Yo is most stretched, and is defined so that its angle increases in an anticlockwise direction from a rightward direction in the figure which is taken as the 0° direction. For example, an image that is most stretched in the vertical direction will be designated by Y90, while an image that is most stretched in the horizontal direction will be designated by Y0.

FIG. 4B shows examples of distorted images Y90 that have been created by stretching a reference image in the vertical direction (i.e. in the 90° direction). The distorted image Y90a is created by stretching the dimension in the vertical direction of the original image Yo, and by shrinking the dimension in the horizontal direction of the original image Yo. Furthermore, the distorted image Y90b is an image in which distortion level is yet higher, and is created by stretching the dimension in the vertical direction of the distorted image Y90a even more, and by shrinking the dimension in the horizontal direction of the distorted image Y90a even more. The distorted images Y90a and Y90b are designated as "LOW" and "HIGH" on the basis of their levels of distortion.

It should be noted that a distorted image Y could also be created by stretching or shrinking the original image Yo in one direction only. In other words, it is not necessary to stretch (or to shrink) the image in one direction while also shrinking (or stretching) the image in the other direction orthogonal thereto.

And FIG. 4C shows examples of distorted images Y0 that have been created by stretching the reference image in the horizontal direction (i.e. in the 0° direction). The distorted image Y0a is created by stretching the dimension in the horizontal direction of the original image Yo, and by shrinking the dimension in the vertical direction of the original image Yo. Furthermore, the distorted image Y0b is an image in which the distortion level is yet higher, and is created by stretching the dimension in the horizontal direction of the distorted image Y0a even more, and by shrinking the dimension in the vertical direction of the distorted image Y0a even more. The distorted images Y0a and Y0b are designated as "LOW" and "HIGH" on the basis of their levels of distortion.

FIGS. 5A, 5B and 5C are figures for explanation of distorted images that have been created for distortion sensitivity testing by stretching or shrinking the original image Yo in slanting directions. FIG. 5A shows the original image Yo for comparison.

FIG. 5B shows two distorted images Y45a and Y45b whose directions of distortion are 45° and whose levels of distortion are respectively "LOW" and "HIGH". The distorted image Y45a is created by stretching the dimension in the 45° direction of the original image Yo, and by shrinking the dimension in the 135° direction of the original image Yo. Furthermore, the distorted image Y45b is created by stretching the dimension in the 45° direction of the distorted image Y45a even more, and by shrinking the dimension in the 135° direction of the distorted image Y45a even more.

And FIG. 5C shows two distorted images Y135a and Y135b whose directions of distortion are 135° and whose levels of distortion are respectively "LOW" and "HIGH". The distorted image Y135a is created by stretching the dimension in the 135° direction of the original image Yo, and by shrinking the dimension in the 45° direction of the original image Yo. Furthermore, the distorted image Y135b is created by stretching the dimension in the 135° direction of the distorted image Y135a even more, and by shrinking the dimension in the 45° direction of the distorted image Y135a even more.

It should be understood that while, in the examples described above, the distorted images Y have symmetry of images obtained by stretching or shrinking the original image Yo in two mutually orthogonal directions, it would also be possible to create a distorted image Y having an irregular distortion that is not symmetrical, with each point in the image being displaced appropriately or the like.

The original image Yo may be an image of any sort. For example, it may be an image of an object that the subject sees on a daily basis, such as a landscape, a portable telephone, a book, a newspaper, a personal computer, a tablet terminal, a musical score, or the like.

The display control unit 511 (refer to FIG. 3) displays a plurality of distorted images Y whose directions of distortion and/or levels of distortion are different upon the display screen 501, while changing over between them. The subject views this plurality of different distorted images Y that are thus displayed, and responds with his impressions of viewing the distorted images Y, such as whether or not he can view them comfortably, whether or not they are acceptable for daily viewing, and so on. On the basis of these responses, the sensitivity of the subject to distortion is evaluated, and is represented by numerical values or grades.

It should be noted that one or more of the distorted images Y may be a moving image.

Figure 6:
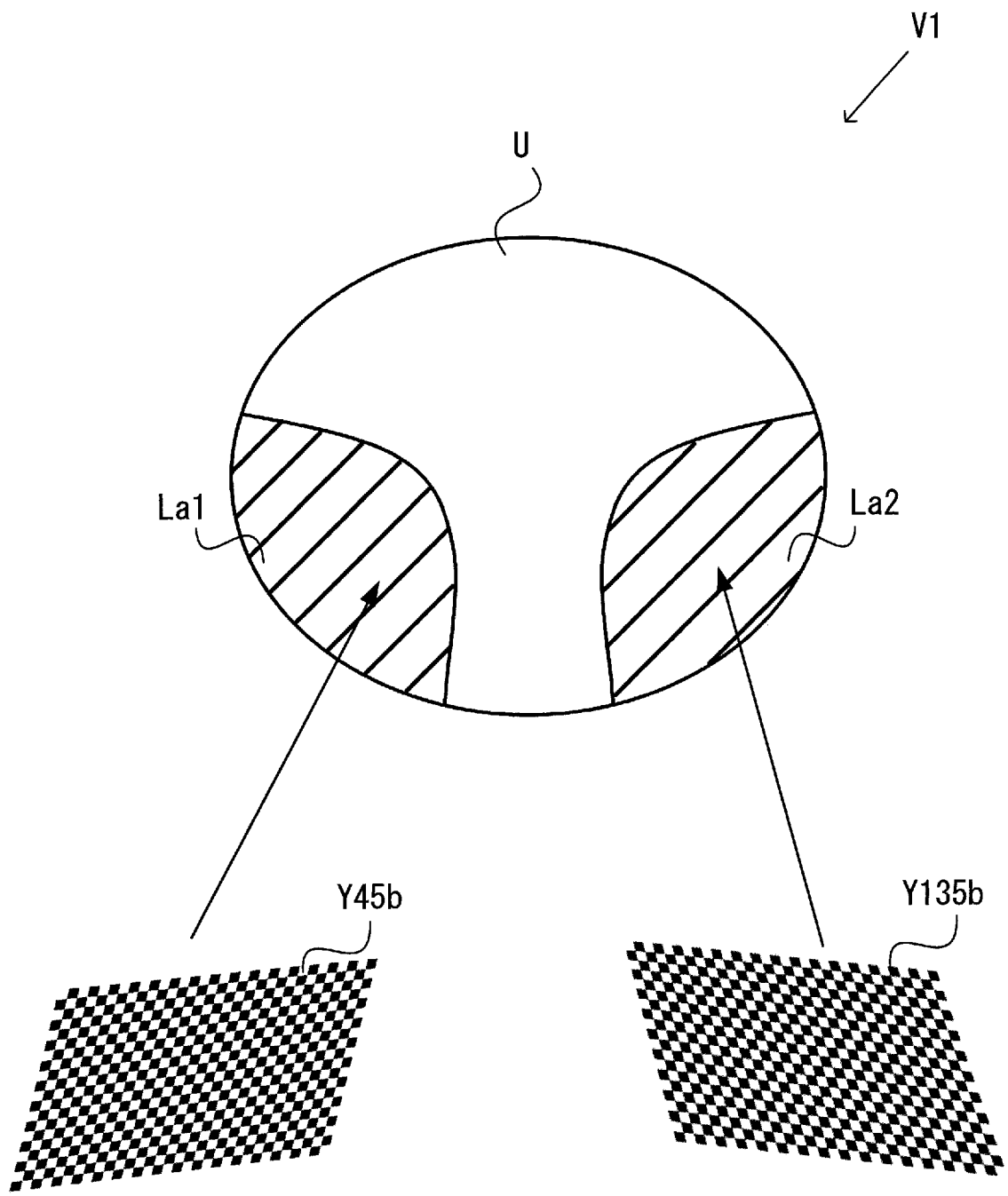
FIG. 6 is a conceptual figure for explanation of positions at which distorted images are presented.

FIG. 6 is a figure for explanation of positions in a field of view of the subject at which a distorted image Y is presented. The display control unit 511 displays distorted images Y as a left eye image 501L and as a right eye image 501R (refer to FIG. 1B) at positions that correspond to side portions La1, La2 when the subject is wearing progressive power lenses. Here, a progressive power lens is an eyeglass lens that comprises a distance area, a near area and an intermediate area that connects the distance area and the near area so that the refractive index changes continuously, with the distance area being disposed above the intermediate area and the near area being disposed below the intermediate area. In the embodiments described below, a distance to be seen through the distance area is termed a long distance, a distance to be seen through the near area is termed a short distance, and a distance to be seen through the intermediate area is termed an intermediate distance. Respective examples of distances corresponding to long distances, intermediate distances, and short distances are long distances of one meter or greater, intermediate distances of fifty centimeters or greater and less than one meter, and short distances of twenty-five centimeters or greater and less than fifty centimeters, but these classifications may be varied as appropriate, according to circumstances.

It should be understood that, apart from regions corresponding to the side portions La1 or La2, the display control unit 511 may display one or more distorted images Y in partial regions of the left eye image 501L and/or the right eye image 501R at any desired positions and over any desired ranges.

In FIG. 6, a field of view corresponding figure V1 has a left side portion La1, a right side portion La2, and a non-side portion U that includes a distance area, a near area, and an intermediate area. The side portions La1 and La2 are indicated by hatching. This field of view corresponding figure V1 explains at what positions in the display image distortion or the like is located by employing an outline of the eyeglass lens and so on. It should be understood that the field of view corresponding figure V1 is also a figure that schematically shows examples of display positions of images, but it would also be possible in a display image to omit the lines and so on that schematically show the outlines of the eyeglass lens and of the side portions La1, La2 of the eyeglass lens, as appropriate.

The display control unit 511 (refer to FIG. 3) calculates regions in the left eye image 501L and the right eye image 501R that correspond to the side portions La1, La2 on the basis of assumed general distances between the display screen 501 (refer to FIG. 1B) and the eyes E of the subject, the vertex distance of the subject, and so on, and disposes the distorted images Y upon those regions. The regions corresponding to the left side portion La1 are disposed more to the left side than the centers of each of the left eye image 501L and the right eye image 501R, and the regions corresponding to the right side portion La2 are disposed more to the right side than the centers of each of the left eye image 501L and the right eye image 501R.

For each of the left eye image 501L and the right eye image 501R, the display control unit 511 displays a distorted image Y45b whose distortion direction is, for example, 45° in the region corresponding to the left side portion La1, and displays a distorted image Y135b whose distortion direction is, for example, 135° in the region corresponding to the right side portion La2. By arranging, in the left side portion La1 and in the right side portion La2, these two distorted images Y having directions of distortion that are angled in symmetrical directions, in other words the sum of whose angles specifying their directions of distortion is 180°, it is possible to present distortion in the field of view of the subject that is similar to the distortion that occurs when he is wearing an actual progressive power lens.

In connection with the value of the angle that specifies the distortion direction, a variation within +10° or −10° may be considered to be acceptable, in view of errors and differences between individuals. However, the difference of angle that is permissible in consideration of variation is not limited to this value. Moreover, the plurality of distorted images Y that are arranged in the regions corresponding to the side portions La1, La2 may have different levels of distortion instead of different directions of distortion, or may have both different levels of distortion and different directions of distortion.

With the method for designing an eyeglass lens of the present embodiment, it is possible to set a target aberration distribution, and/or a target power distribution, or a value of the upper permitted limit of aberration at one or a plurality of points upon the eyeglass lens being designed, on the basis of information that has been obtained by distortion sensitivity testing, and the information is related to the sensitivity to distortion of the subject or, in other words, a wearer of the eyeglass lens being designed. In particular, it is preferable to set the target aberration and the value of the upper permitted limit of aberration for astigmatism.

An eyeglass lens ordering and order receiving system relating to the design of an eyeglass lens will now be explained. The eyeglass lens ordering and order receiving system according to the present embodiment is capable of providing an eyeglass lens for which the optical characteristics such as aberration and so on have been appropriately set according to the sensitivity of the wearer to distortion in the visual field of the wearer, as described above.

Figure 7:
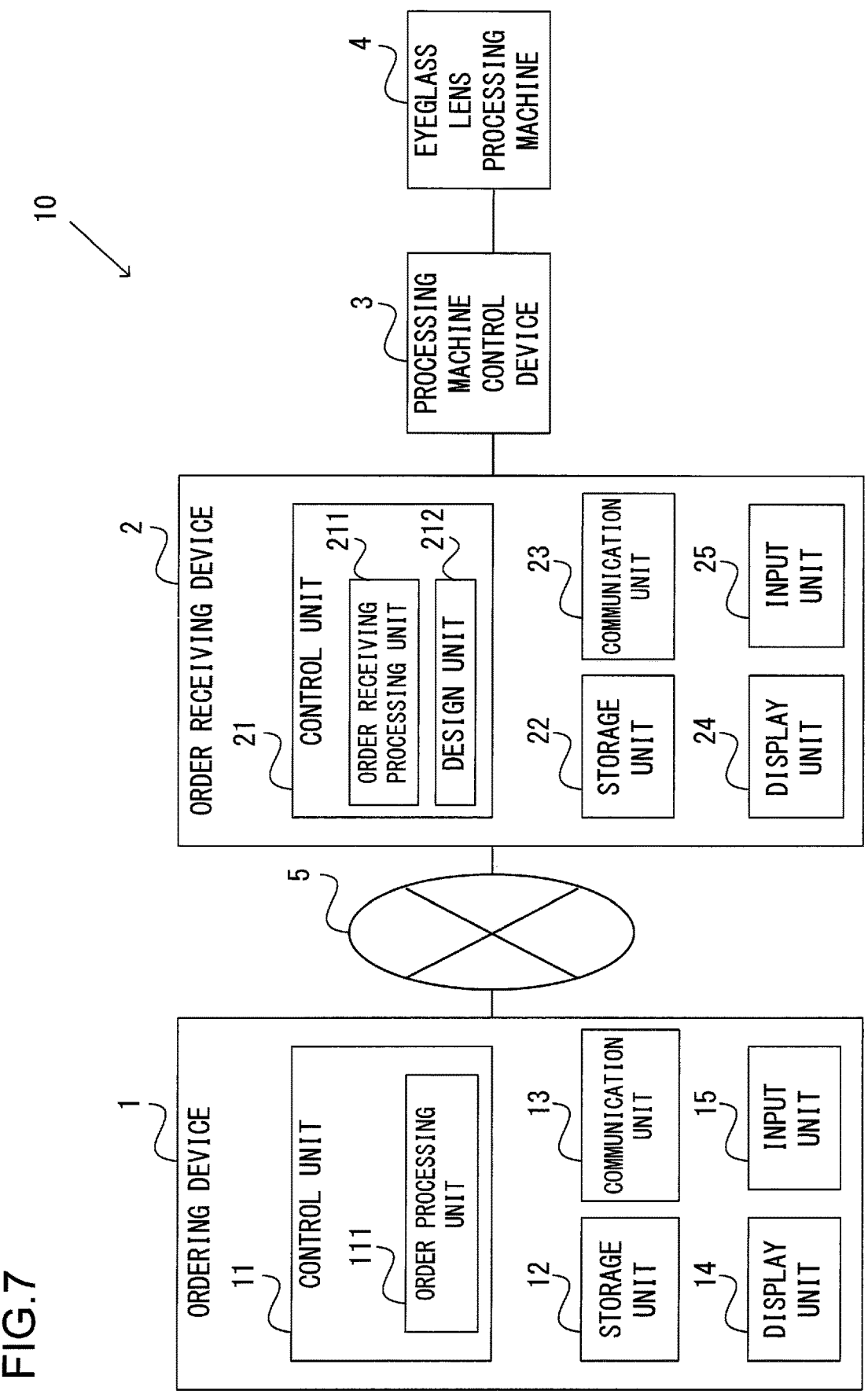
FIG. 7 is a conceptual figure showing the configuration of an eyeglass lens ordering and order receiving system.

FIG. 7 is a figure showing the configuration of the eyeglass lens ordering and order receiving system 10 according to the present embodiment. This eyeglass lens ordering and order receiving system 10 comprises an ordering device 1 that is installed at an eyeglass shop (i.e. at an ordering entity), and an order receiving device 2, a processing machine control device 3, and an eyeglass lens processing machine 4 that are installed at a lens manufacturer. The ordering device 1 and the order receiving device 2 are connected together via a network 5 such as, for example, the internet or the like, so as to be capable of mutual communication. Moreover, the processing machine control device 3 is connected to the order receiving device 2, and the eyeglass lens processing machine 4 is connected to the processing machine control device 3. It should be understood that, for the convenience of illustration, only a single ordering device 1 is shown in FIG. 7, but actually a plurality of ordering devices 1 that are installed in a plurality of eyeglass shops may be connected to the order receiving device 2.

The ordering device 1 is a computer that performs order processing for eyeglass lenses, and comprises a control unit 11, a storage unit 12, a communication unit 13, a display unit 14, and an input unit 15. The control unit 11 comprises a processor such as a CPU or the like, and controls the ordering device 1 by executing a program stored in the storage unit 12. The control unit 11 comprises an order processing unit 111 that performs eyeglass lens order processing. The communication unit 13 performs communication with the order receiving device 2 via the network 5. The display unit 14 is a display device such as a liquid crystal display or a CRT or the like, and displays an ordering screen and so on for input of information for ordering eyeglass lenses (i.e., order information). And the input unit 15 comprises input devices such as a mouse, a keyboard or the like. Order information and so on is inputted via the input unit 15 according to the details upon the ordering screen.

It should be understood that the display unit 14 and the input unit 15 may be provided as one integral structure by employing a touch panel or the like.

The order receiving device 2 is a computer that performs processing for receiving orders for eyeglass lenses, design processing, optical performance calculation processing, and so on, and comprises a control unit 21, a storage unit 22, a communication unit 23, a display unit 24, and an input unit 25. The control unit 21 comprises a processor such as a CPU or the like, and controls the order receiving device 2 by executing a program stored in the storage unit 22. The control unit 21 comprises an order receiving processing unit 211 that performs eyeglass lens order receiving processing, and a design unit 212 that performs eyeglass lens design processing. The communication unit 23 performs communication with the ordering device 1 via the network 5, and also performs communication with the processing machine control device 3. The storage unit 22 stores data for various types of eyeglass design, so that it can be read out. The display unit 24 is a display device such as a liquid crystal display or a CRT or the like, and displays the results of designing eyeglass lenses and so on. And the input unit 25 comprises input devices such as a mouse and a keyboard and so on.

Incidentally, the display unit 24 and the input unit 25 may be provided as one integral structure by employing a touch panel or the like. Moreover, the functions of the order receiving device 2 may be performed by an order reception device that comprises the order receiving processing unit 211 and by a design device that comprises the design unit 212.

Figure 8:
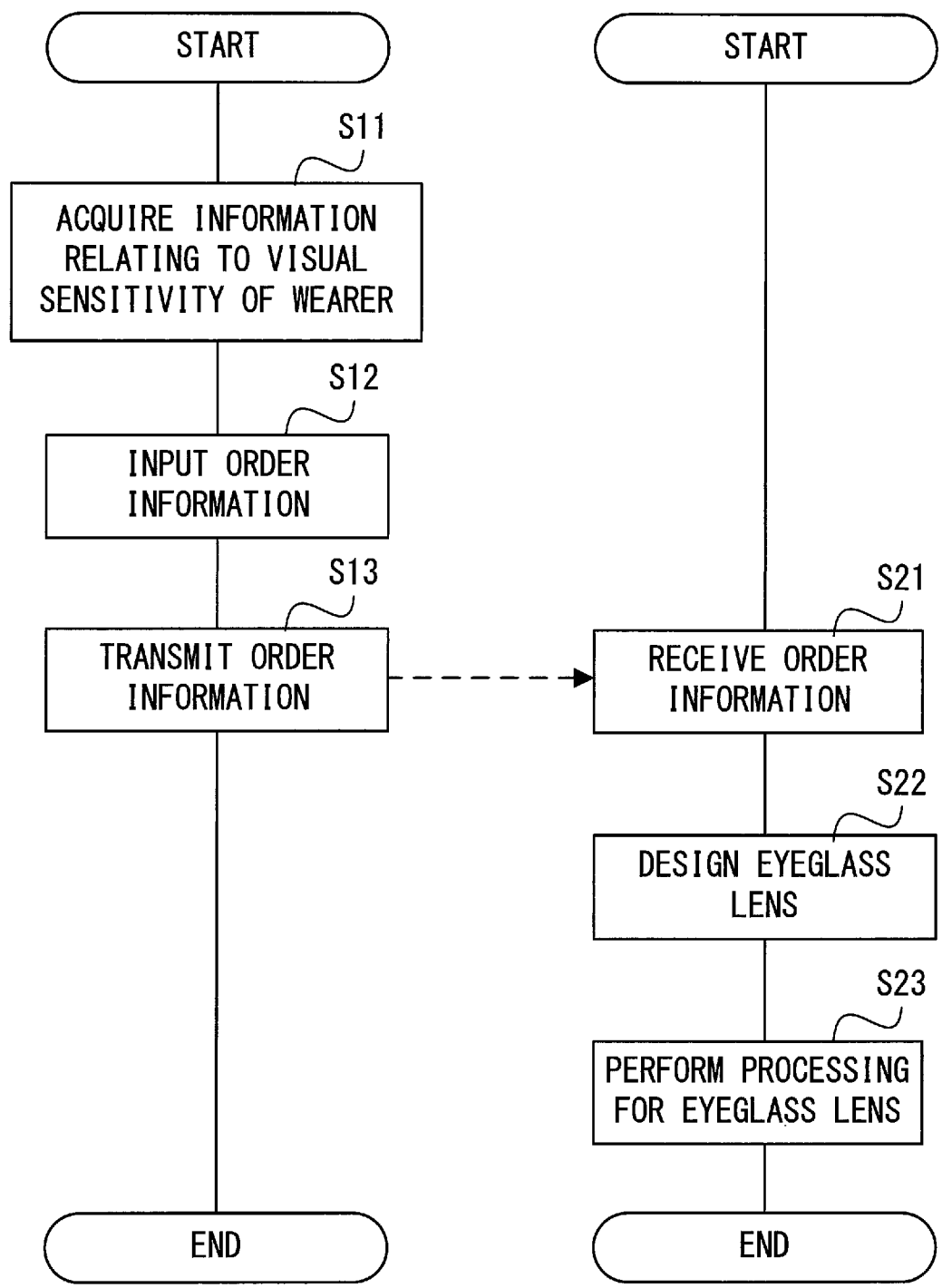
FIG. 8 is a flow chart showing flow of a method for designing an eyeglass lens according to the embodiment.

Next, the procedure for supply of an eyeglass lens by the eyeglass lens ordering and order receiving system 10 will be explained using the flow chart shown in FIG. 8. The steps S11 through S13 shown on the left side of FIG. 8 are performed on the side of the eyeglass shop, while the steps S21 through S23 shown on the right side of FIG. 8 are performed on the side of the lens manufacturer. In the method for manufacturing an eyeglass lens implemented by this eyeglass lens ordering and order receiving system 10, the eyeglass lens is designed by the method for designing an eyeglass lens described above.

In a step S11, the ordering entity acquires information relating to the visual sensitivity of a wearer. In the present embodiment, as shown in FIG. 9, the ordering entity performs distortion sensitivity testing while taking the wearer as subject, and acquires the above information relating to the sensitivity of the wearer to distortion.

Figure 9:
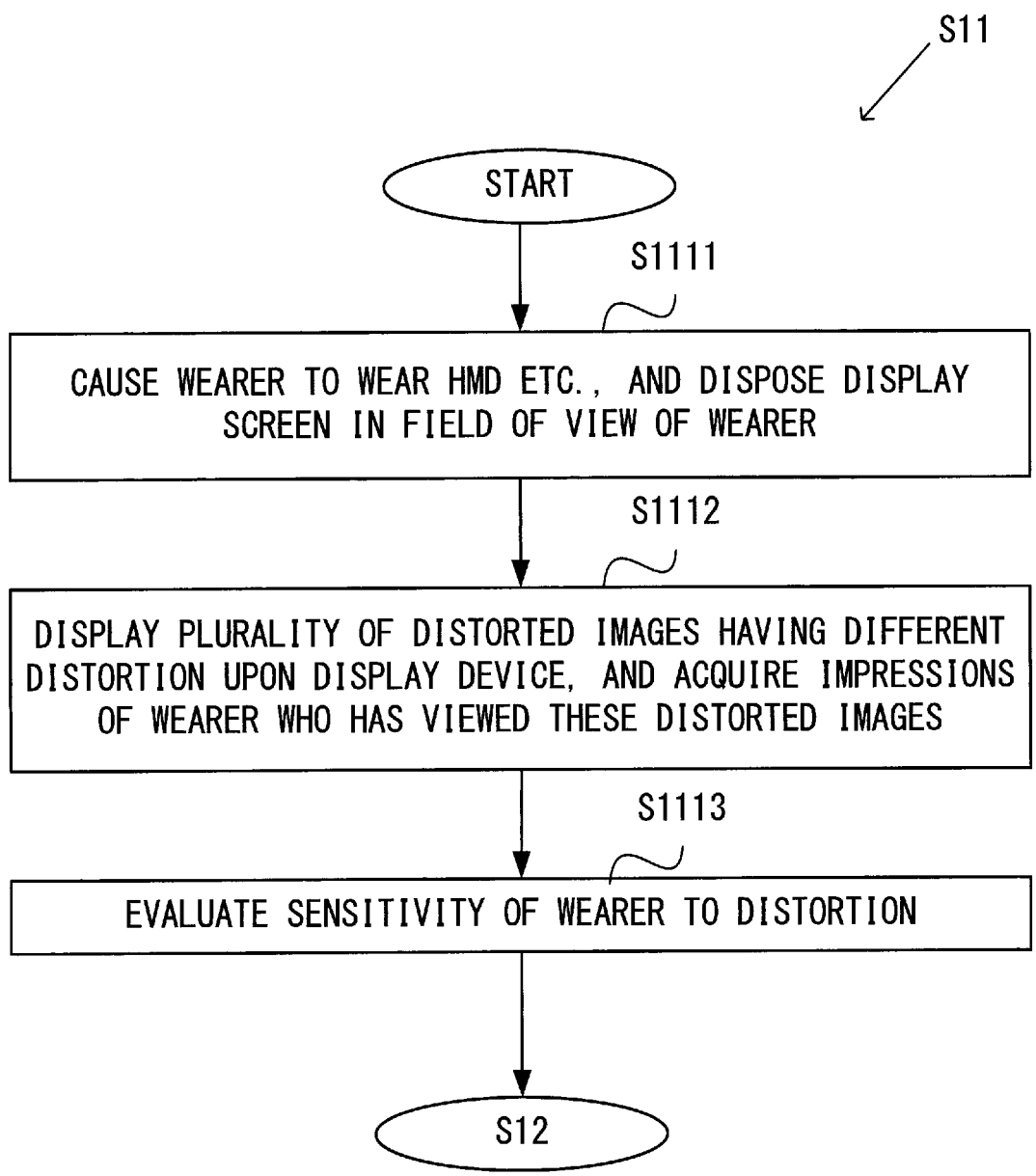
FIG. 9 is a flow chart showing the flow of a method for designing an eyeglass lens according to the embodiment.

FIG. 9 is a flow chart showing the step S11 further subdivided into a plurality of steps. In a step S1111, the ordering entity causes the wearer to wear the display device 50 such as an HMD or the like, and disposes the display screen 501 in the field of view of the wearer. When this step S1111 is completed, a step S1112 is started.

In a step S1112, the ordering entity sequentially displays a plurality of distorted images Y having different distortions upon the display screen 501 and causes the wearer to view them, and thereby acquires the impressions of the wearer who views these distorted images Y. As shown in FIG. 6, the ordering entity displays distorted images Y in the regions of the display screen 501 that corresponding to the side portions La1, La2 of a progressive power lens. And the ordering entity progressively increases the distortion level while keeping the distortion direction of the distorted image Y fixed, and specifies that distorted image Y for which the wearer responds that this distorted image Y is not acceptable. Furthermore, in a condition in which the direction of the distortion is changed, by keeping the distortion direction fixed in the changed condition, and by increasing the distortion level, that distorted image Y is specified for which the wearer responds that this distorted image Y is not acceptable. In this manner, for one or a plurality of directions of distortion, a plurality of distorted images Y are displayed each having a different distortion level. When this step S1112 is completed, a step S1113 is started.

It should be understood that the order in which the distorted images Y having different levels of distortion are presented is not particularly limited. Distorted images Y whose levels of distortion are sufficiently small to be acceptable to the wearer can be presented once in every few images, so that the wearer does not become habituated to the distortion.

In the step S1113, the ordering entity evaluates the sensitivity of the wearer who has viewed the distorted images Y to distortion in the field of view of the wearer. The ordering entity converts the sensitivity of the wearer to distortion, obtained in the step S1112 on the basis of the response from the wearer who has viewed the distorted images Y, to a numerical value according to a predetermined standard, and records this numerical value. For example if, as described above, the distortion level of the distorted image Y is increased until the wearer responds that it is not acceptable, then the distortion level of the distorted image Y for which the wearer first responds that it is not acceptable, or the distortion level of the distorted image Y that the wearer is last able to accept, is acquired as being a parameter that specifies the sensitivity of the wearer to distortion (hereinafter this is termed the "sensitivity parameter"). In other words, the sensitivity parameter is determined on the basis of the distorted images specified as described above. When this step S1113 is completed, a step S12 is started.

In the step S12, the ordering entity determines eyeglass lens order information, including the information relating to the sensitivity of the wearer to distortion in the field of view of the wearer, such as the sensitivity parameter acquired in the step S1113 and so on. And the ordering entity causes the display unit 14 of the ordering device 1 to display an ordering screen, and inputs order information via the input unit 15.

FIG. 10 is a figure showing an example of an ordering screen 100a. Order information is displayed upon this ordering screen 100a, separated into items. In a lens information item 101, items relating to power of the lenses ordered, such as a product name, spherical power (i.e. the S power), astigmatic power (i.e. the C power), an astigmatic axis angle, addition, and so on are inputted. A processing specification information item 102 is inputted when specifying an external diameter of the lens being ordered, or when specifying its thickness at some arbitrary point. A tinting information item 103 is inputted when specifying a color for the lens. Information about the position of the eyes of the wearer is inputted as a fitting point (FP) information item 104. PD represents the pupillary distance. The frame model name and the frame classification and so on are inputted as a frame information item 105. And numerical values specifying intensity of the sensitivity of the wearer to distortion, such as sensitivity parameters obtained during distortion sensitivity testing and so on, are inputted as a sensitivity information item 106a.

In the example of FIG. 10, for each distortion direction, the intensity of sensitivity to distortion is specified by a numerical value in ten steps (in this example, this value is "4" for 0°, "5" for 45°, and so on). In the example of FIG. 10, the intensity of the sensitivity to distortion is defined so that the sensitivity to distortion becomes greater, the larger is the numerical value representing it. In other words, the intensity of the sensitivity here indicates strength of resistance to distortion. In this case, for example, the sensitivity parameter is set as follows. The distorted image Y created with the minimum distortion level is classified as Category 1, the distorted image Y created with the maximum distortion level is classified as Category 10, and thus the distorted images Y are classified into ten levels according to their levels of distortion. And the classification of the distorted image Y having the maximum limit of distortion that the wearer can tolerate is taken as being a measured value of the intensity of the sensitivity.

In terms of the way the sensitivity to distortion is expressed, it would also be possible to arrange for the numerical value to become greater, the smaller is the sensitivity to distortion. In this case, the intensity of the sensitivity indicates susceptibility of the wearer, and, if even a small amount of distortion is not acceptable, then the numerical value becomes high since the susceptibility is high. Moreover, the measured value of the intensity of the sensitivity may be defined, not as a numerical value, but as a symbol; indeed, the method is not particularly limited, provided that the sensitivity to distortion can be defined according to a standard that is determined in advance.

It should be understood that, apart from the items described above, it would also be possible to add other information of various kinds upon the ordering screen 100a, such as fitting parameters like a pantoscopic angle of a frame, a warp angle, and the vertex distance, or information relating to power of accommodation of the wearer. Furthermore, in addition to or instead of the numerical value that specifies the intensity of the sensitivity of the wearer to distortion, it would also be possible to arrange for a design parameter to be inputted such as an index indicating a range in the eyeglass lens being designed where astigmatism is small. In the eyeglass lens, as the index indicating a range where astigmatism is small, for example, it is possible to set a length in the horizontal direction or the like where astigmatism becomes less than or equal to a predetermined value at a predetermined height in the distance area or in the near area, as shown by arrow signs in a broken line or in a single dotted chain line in FIG. 12, as will be explained hereinafter, When the ordering entity inputs each item upon the ordering screen 100a of FIG. 10 and clicks upon a send button (not shown in the figure), then the order processing unit 111 of the ordering device 1 acquires the information that has been inputted for each item upon the ordering screen 100a (i.e., the order information), and a step S13 (refer to FIG. 8) is started. In the step S13, the ordering device 1 transmits this order information to the order receiving device 2 via the communication unit 13.

In the ordering device 1, processing for displaying the ordering screen 100a, processing for acquiring the order information inputted via the ordering screen 100a, and processing for transmitting that order information to the order receiving device 2 are performed by the control unit 11 of the ordering device 1 executing a predetermined program that is installed in advance in the storage unit 12.

Upon receipt of the order information from the ordering device 1 by the order receiving processing unit 211 of the order receiving device 2 in a step S21 (refer to FIG. 8), a step S22 is started. And, in the step S22, the design unit 212 of the order receiving device 2 performs design of the eyeglass lens on the basis of the order information that has thus been received.

Figure 11:
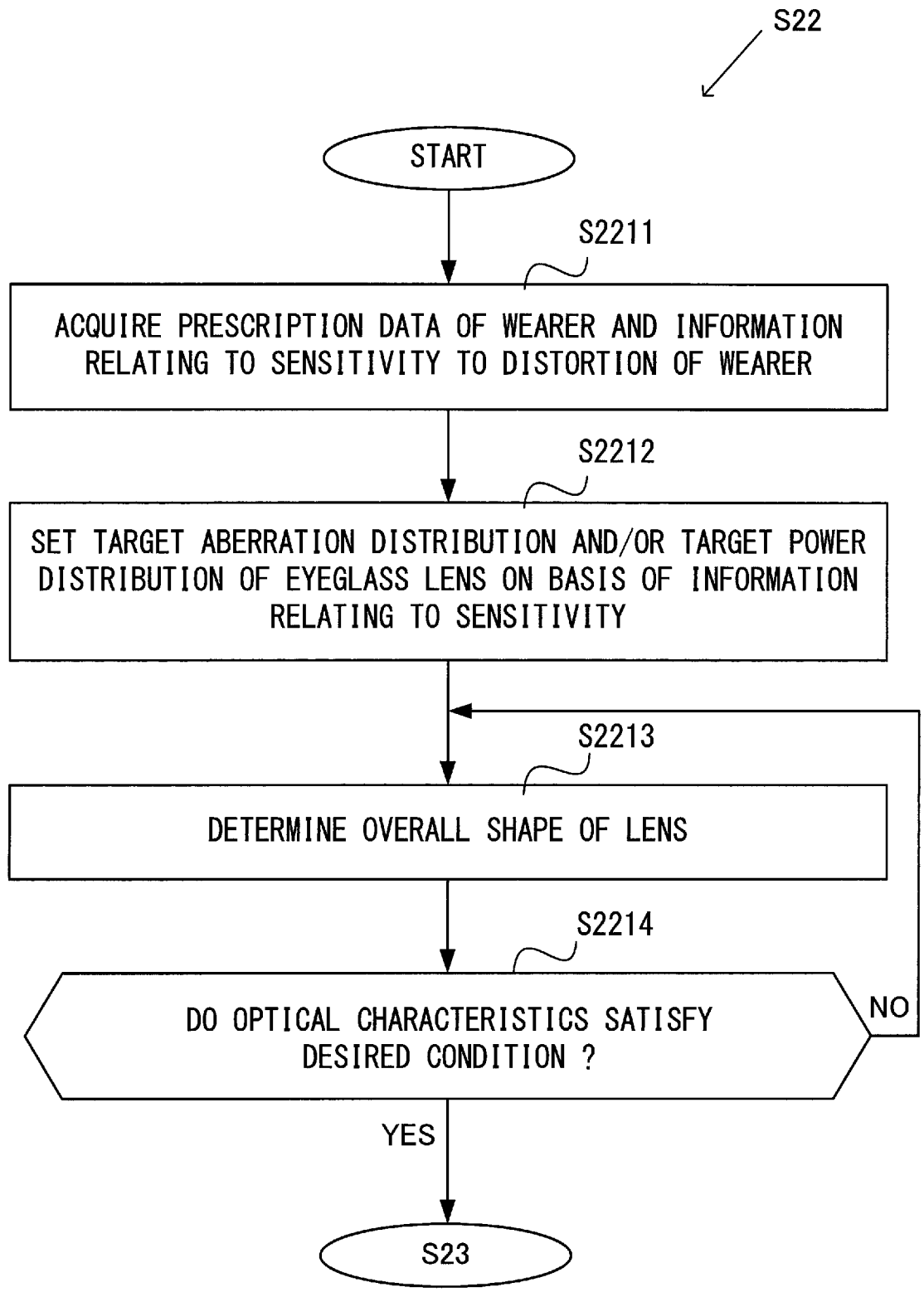
FIG. 11 is a flow chart showing the flow of a method for designing an eyeglass lens according to the embodiment.

FIG. 11 is a flow chart showing the procedure for design of the eyeglass lens corresponding to the step S22. In the step S2211, the order receiving device 2 acquires prescription data for the eyeglass lens and the information relating to the sensitivity of the wearer to distortion and/or the design parameters such as the index indicating a range where astigmatism is small. The order receiving device 2 also acquires fitting parameters, such as the pantoscopic angle, the warp angle, the vertex distance, or the like, as appropriate. When the step S2211 is completed, a step S2212 is started.

In the step S2212, the design unit 212 of the order receiving device 2 sets the target aberration distribution and/or the target power distribution of the eyeglass lens on the basis of the information relating to the sensitivity of the wearer to distortion and/or the design parameters, that were acquired in the step S2211.

Figure 12:
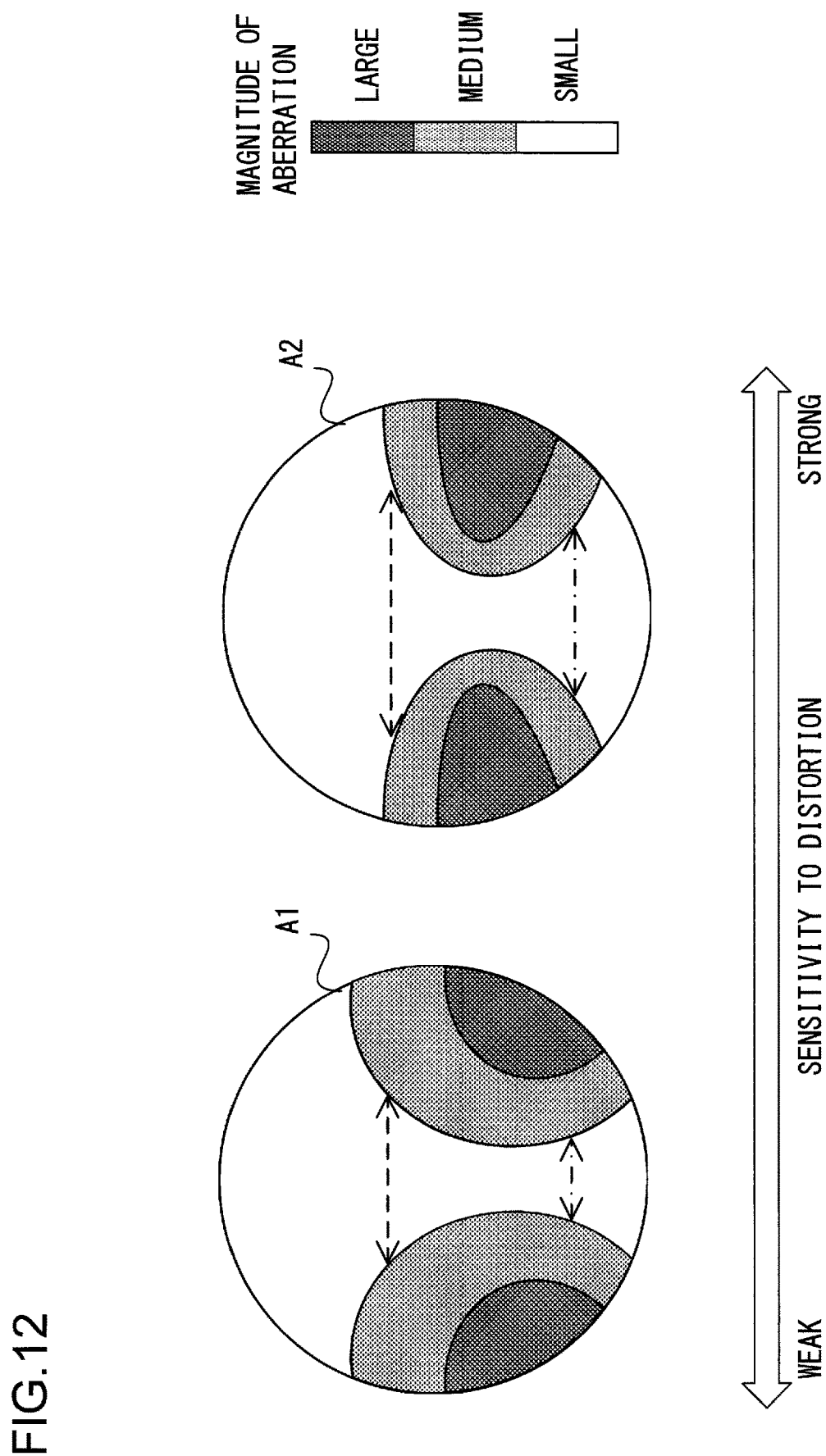
FIG. 12 is a figure schematically showing distributions of aberration upon an eyeglass lens being designed.

FIG. 12 is a conceptual figure showing an example of setting a target aberration in relation to astigmatism on the basis of the sensitivity of the wearer to distortion. Two aberration distribution diagrams A1, A2 are shown at the center of this figure, and, at a part of the figure at the rightmost side, the magnitude of aberration corresponding to each of patterns used for specifying the magnitude of aberration in the aberration distribution diagram is shown. The arrow signs in the broken line indicate widths of portions where the magnitude of the aberration is less than or equal to a predetermined value, as described above. It should be understood that the predetermined value may be any appropriate value that is determined in advance; for example, a value such as 0.5 diopters may be considered, but the actual value is not limited to this. In each aberration distribution diagram, the upper broken line arrow sign indicates a width of a portion in the distance area where the magnitude of the aberration is less than or equal to a predetermined value, and this width can be employed as an index for designing the distance area. Moreover, the lower single dotted chain line arrow sign indicates a width of a portion in the near area where the magnitude of the aberration is less than or equal to a predetermined value. This width can be employed as an index for designing the near area. The positions in the vertical direction of the broken line arrow sign and the single dotted chain line arrow sign may be set as desired; for example, these positions may be determined according to a position of a far vision measurement point (i.e. a distance power measurement position) or a position of a near vision measurement point (i.e. a near power measurement position) as reference.

In the aberration distribution diagram shown in FIG. 12, the aberration distribution diagram A1 on the left side shows a lens for a wearer whose sensitivity to distortion is weak. With a lens of this sort, although a range where astigmatism is small is narrow, the distortion level is small since the change of astigmatism is small. On the other hand, the aberration distribution diagram A2 on the right side shows a lens for a wearer whose sensitivity to distortion is stronger than in the case of the aberration distribution diagram A1. With a lens of this sort, although the change in astigmatism is large, ranges where astigmatism is small in the distance area and in the near area are designed to be wider than in the case of the aberration distribution diagram A1. When the step S2212 has been completed, a step S2213 is started.

In the step S2213 (refer to FIG. 11), the order receiving device 2 determines an overall lens shape of an entire eyeglass lens on the basis of the target aberration distribution and/or the target power distribution that have been set. When the step S2213 has been completed, a step S2214 is started. In the step S2214, the order receiving device 2 makes a decision as to whether or not the optical characteristics of the eyeglass lens, such as its refractive power, its astigmatism, and so on, satisfy a desired condition. Such a desired condition is a condition that satisfies all the items of the prescription while reflecting the sensitivity of the wearer. If the desired condition is satisfied, then an affirmative decision is reached in the step S2214 and the design processing terminates, and a step S23 (refer to FIG. 8) is started. But if the desired condition is not satisfied, then a negative decision is reached in the step S2214, and the step S2213 is started again.

In the step S23, the order receiving device 2 outputs the design data for the eyeglass lens that have been designed in the step S22 to the processing machine control device 3. And, on the basis of this design data that have been outputted from the order receiving device 2, the processing machine control device 3 sends processing commands to the eyeglass lens processing machine 4. As a result, an eyeglass lens is processed and is manufactured by the eyeglass lens processing machine 4 on the basis of the above design data. The eyeglass lens that has thus been manufactured by the eyeglass lens processing machine 4 is shipped to the eyeglass shop, and is fitted into an eyeglass frame and is supplied to the client (i.e. to the wearer).

It should be understood that, regarding the order receiving device 2, the processing for receiving the order information from the ordering device 1, the processing for designing the eyeglass lens on the basis of the order information that has thus been received, and the processing for outputting the design data for the eyeglass lens to the processing machine control device 3, are all performed by the control unit 21 of the order receiving device 2 executing a predetermined program that is installed in advance in the storage unit 22.

According to the embodiment described above, the following beneficial operational effects are obtained.

(1) The method for designing an eyeglass lens of the present embodiment comprises displaying the distorted image Y upon the display device 50 while maintaining the positional relationship of the face of the subject and the display device 50, and acquiring information in which the visual sensitivity of the subject is evaluated on the basis of an impression received by the subject who has viewed the distorted images Y.

Due to this, it is possible to measure the visual sensitivity of the wearer in an accurate manner by presenting the image in a desired position based upon the eye of the wearer, so that it is possible to design an eyeglass lens that is well matched to the wearer on the basis of that sensitivity.

(2) In the method for designing an eyeglass lens of the present embodiment, the display device 50 may be disposed at a position based upon the height of the eye of the subject. Due to this, it is possible to present the image at a desired position that is matched to the eye of the subject, so that it is possible to measure the visual sensitivity of the subject in an accurate manner.

(3) In the method for designing an eyeglass lens of the present embodiment, in the display of the image by the display device 50, a plurality of distorted images Y are displayed having different distortion; and, in the evaluation of the sensitivity, the sensitivity of the subject to distortion is evaluated on the basis of the impressions received by the subject who has viewed the plurality of distorted images Y. Due to this, it is possible to design an eyeglass lens that is matched to the wearer on the basis of the sensitivity of the wearer to distortion.

(4) In the method for designing an eyeglass lens of the present embodiment, the plurality of distorted images Y displayed upon the display device 50 differ by at least one of distortion level and distortion direction of the distortion. Due to this, from the reaction of the wearer to distorted images Y of various kinds, it is possible to measure the sensitivity of the wearer to distortion more accurately.

(5) In the method for designing an eyeglass lens of the present embodiment, each of the distorted images Y is distorted in one or a plurality of partial regions. Due to this, it is possible to measure the sensitivity of the wearer to distortion in a part of the field of view of the wearer in accordance with the structure of the eyeglass lens such as a progressive power lens or the like.

(6) In the method for designing an eyeglass lens of the present embodiment, in each of the plurality of partial regions, the distorted images Y are mutually different with regard to at least one of distortion level and distortion direction. Due to this, it is possible to measure the sensitivity of the wearer to distortion on the basis of the type of distortion of the eyeglass lens such as a progressive power lens or the like, which can easily appear depending upon the position within the lens.

(7) In the method for designing an eyeglass lens of the present embodiment, each of the distorted images Y is distorted both in a partial region on the left side from the center of the distorted image Y, and in a partial region on the right side from the center of the distorted image Y. Due to this, it is possible to measure the sensitivity of the wearer to distortion on the basis of the positions upon the eyeglass lens where distortion can easily occur or the like, such as the side portions La1, La2 or the like of a progressive power lens.

(8) The eyeglass lens ordering device 1 according to the present embodiment comprises the input unit 15 that inputs information in which visual sensitivity of the subject that is evaluated on the basis of an impression received by the subject who has viewed the distorted image Y that has been displayed while maintaining the positional relationship between the face of the subject and the display device, and the communication unit 13 that transmits the information inputted via the input unit 15, or a design parameter calculated on the basis of that information, to the eyeglass lens order receiving device. Due to this, it is possible to order an eyeglass lens that is matched to the wearer on the basis of the sensitivity of the wearer that is measured in an accurate manner by presenting the image at a desired position while taking the eye of the wearer as a reference.

(9) The eyeglass lens order receiving device 2 according to the present embodiment comprises the reception unit that receives information relating to the visual sensitivity of the subject, or a design parameter calculated on the basis of that information, evaluated on the basis of an impression received by the subject who has viewed the distorted images Y that has been displayed while maintaining the positional relationship between the face of the subject and the display device 50, and the design unit that designs an eyeglass lens on the basis of the information or the design parameter. Due to this, it is possible to receive an order for an eyeglass lens that is matched to the wearer on the basis of the sensitivity of the wearer that is measured in an accurate manner by presenting images at a desired position while taking the eye of the wearer as a reference.

(10) And the eyeglass lens ordering and order receiving system 2 according to the present embodiment comprises the eyeglass lens ordering device 1 described above and the eyeglass lens order receiving device 2 described above. Due to this, it is possible to provide an eyeglass lens that is matched to the wearer on the basis of the sensitivity of the wearer that is measured in an accurate manner by presenting the image at a desired position while taking the eye of the wearer as a reference.

The following variations also come within the scope of the present invention, and can also be combined with the embodiment described above. To elements that are the same as elements of the embodiment described above, the same reference symbols are appended, and explanation thereof will be omitted as appropriate, since they have the same functions.

Variation 1

In the embodiment described above, an example has been explained in which distorted images Y are displayed in regions of the display screen 501 corresponding to the side portions La1, La2 of the progressive power lens, but it would also be possible to present distorted images over the entire extent of the eyeglass lens. Due to this, it becomes simple and easy to measure general sensitivity of the wearer to distortion.

Variation 2

It would also be possible for a distorted image Y for the left eye image 501L and a distorted image Y for the right eye image 501R to have different distortions. In other words, a left eye image 501L and a right eye image 501R that are mutually different may be displayed to the left eye and the right eye of the subject. For example, it would be possible to arrange for the left eye image 501L to have a distortion direction of 45°, and for the right eye image 501R to have a distortion direction of 135°. Due to this, it is possible to impart a feeling like wobbling to the subject, rather than mere visual distortion.

With this type of sensation, it is possible to measure the sensitivity of the subject to distortion in a more accurate manner by observing the reaction of the subject while varying the distorted images Y along with movement of the head of the subject, by movement detection as will be described hereinafter.

Variation 3

It would also be acceptable to provide parallax between the left eye image 501L and the right eye image 501R for enabling stereoscopic vision. Thus, on the basis of the depths of various portions of the object appearing in images in the left eye image 501L and in the right eye image 501R, the portions of the images in the left eye image 501L and the right eye image 501R corresponding to these portions are displaced, so that stereoscopic vision becomes possible. Due to this, it is possible to measure the visual sensitivity of the wearer in a more accurate manner by taking stereoscopic vision into account.

Variation 4

The distorted image Y may be a processed image obtained by processing one or more images that have been captured by imaging at least a part of the surroundings of the subject for distortion sensitivity testing.

Figure 13:
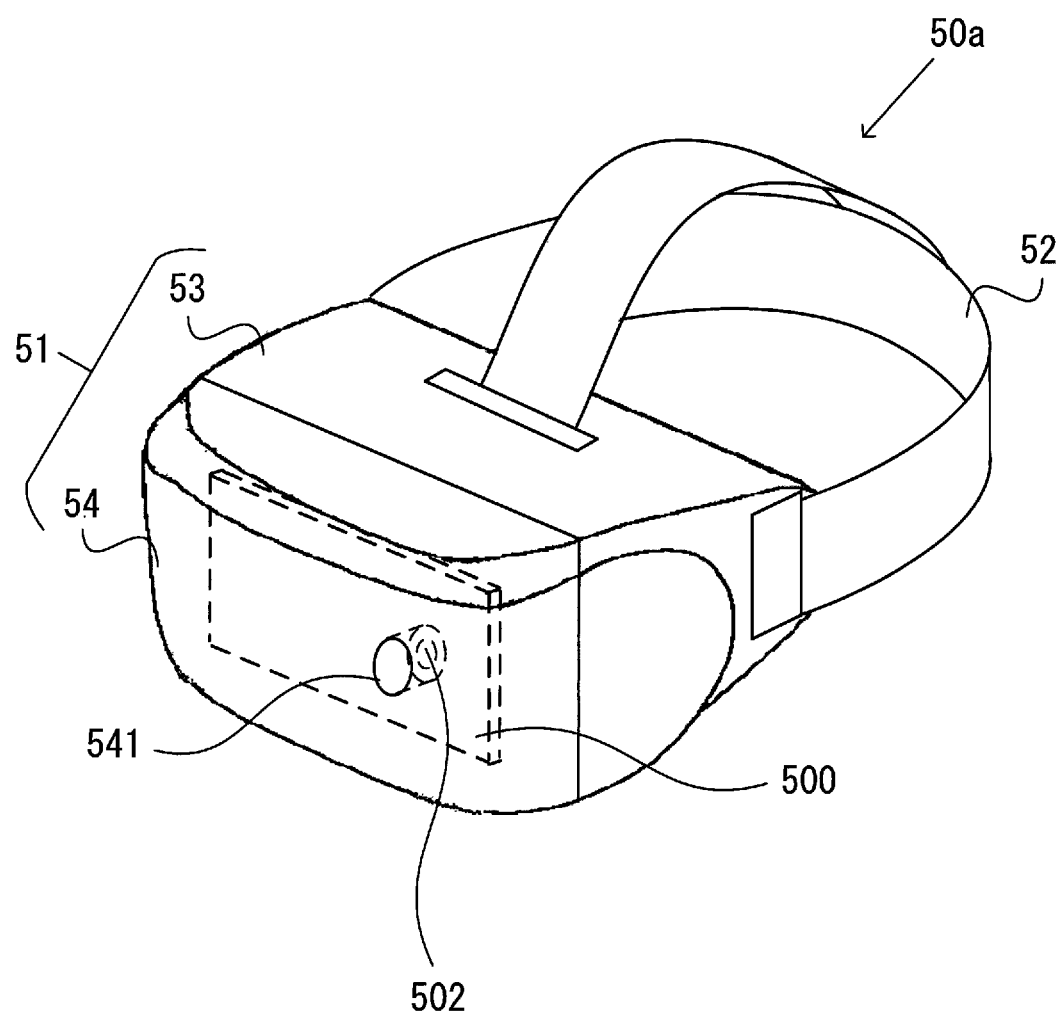
FIG. 13 is a perspective view showing a display device.

FIG. 13 is a perspective view showing a display device 50a that processes and displays an image obtained by capturing the exterior. An opening portion 541 is formed in a cover of the display screen holding unit 54 of the main body 51 of the display device 50a at a position corresponding to a camera 502 of the portable terminal 500. The portable terminal 500 adds distortion to the image of the surroundings of the subject captured through this opening portion 541 by the method shown in the embodiment described above or the like, and displays the resultant image upon the display screen 501. With a method of this type, it is possible to measure the visual sensitivity of the wearer in a more accurate manner on the basis of an image of actual objects.

It should be understood that it would also be possible to capture an image of the surroundings by employing some image capturing device other than the camera of the portable terminal 500. For example, a camera may be provided to the main body 51 itself of the display device 50a.

Variation 5

It would also be possible to arrange for the display device 50 to construct a three dimensional virtual reality space, and to create and display a distorted image Y by taking, as the original image Yo, scenery within this three dimensional virtual reality space corresponding to the direction in which the subject is looking, calculated on the basis of an orientation, an angle, and/or an angular velocity of the portable terminal 500 as detected by the angle detection unit 502. In this case, the distorted image Y is a processed image that has been obtained by processing the image showing the virtual space. Due to this, it is possible to simulate situations of various types by employing a virtual reality space even in a limited space such as an eyeglass shop and measure the visual sensitivity of the wearer.

The display device 50 may be configured to perform movement detection by detecting movement of the head of the subject on the basis of the orientation, the angle, and/or the angular velocity of the portable terminal 500 as detected by the angle detection unit 502, and thereby is able to change the distorted images Y shown upon the display screen 501 on the basis of movement of the subject that has thus been detected. Due to this, it is possible to acquire the impressions of the subject while performing the movements of daily life and so on, so that it is possible to measure the visual sensitivity of the wearer in a greater variety of situations.

The Second Embodiment

A display device 50 and an eyeglass lens ordering and order receiving system 10 according to the second embodiment have configurations similar to those of the display device 50 and the eyeglass lens ordering and order receiving system 10 according to the first embodiment, but the display device 50 differs from the first embodiment in the feature that it displays, not distorted images Y, but an image that includes blurring.

Elements that are the same as elements of the first embodiment will be referred to by the same reference symbols as in the first embodiment, and explanation thereof will be omitted, depending upon each case.

It should be understood that, as the display device, it would be possible to employ an optically transmissive type HMD including a display element that, along with partially transmitting light, is capable of displaying a screen image, so as to be capable of displaying a scene viewed through that HMD in a blurred manner.

With this method for designing an eyeglass lens according to the second embodiment: a wearer of an eyeglass lens to be designed is caused to view images that include different ranges of blurring (hereinafter termed "blurred images"); information is acquired in which visual sensitivity to blurring, and in particular to the range of such blurring is evaluated; and the eyeglass lens is designed on the basis of that information. In the following, this testing for evaluating the sensitivity of the wearer to blurring will be termed "blurring sensitivity testing".

In the following embodiment, "blurring" refers to loss of details of an object that happens when the object is recognized with a resolution that is lower than the appropriate resolution for viewing that object. In more concrete terms, "blurring" principally refers to uncleamess of the outline or pattern that is seen upon viewing an image that has been captured in a defocused state (i.e. a state in which the focus is incorrect), or an image when, due to optical aberration of the ocular system, a focusing plane is deviated away from a retina of the subject.

Figure 14A:
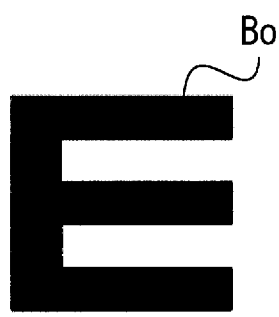
FIG. 14A is a conceptual figure showing an image before blurring.
Figure 14B:
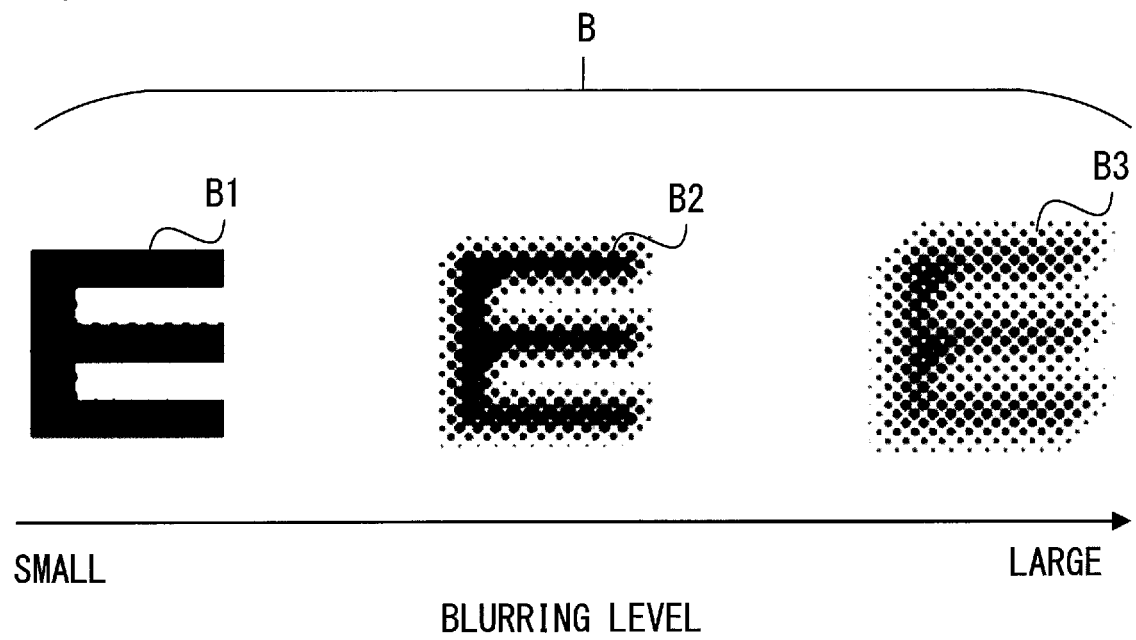
FIG. 14B is a conceptual figure showing blurred images in which blurring levels are varied.

FIGS. 14A and 14B are figures showing an original image Bo and a blurred image B resulting from processing of that original image Bo. As this example of an original image Bo, FIG. 14A shows an image consisting of an alphabetic letter "E". And FIG. 14B is a figure showing three blurred images B1, B2, and B3 that have been created by adding blurring of three types to the original image Bo, in order of increasing level of blurring (hereinafter termed "blurring level"). It will be understood that, the greater is the blurring level, the less clear the position and shape of the outline of the blurred image becomes.

Figure 15A:
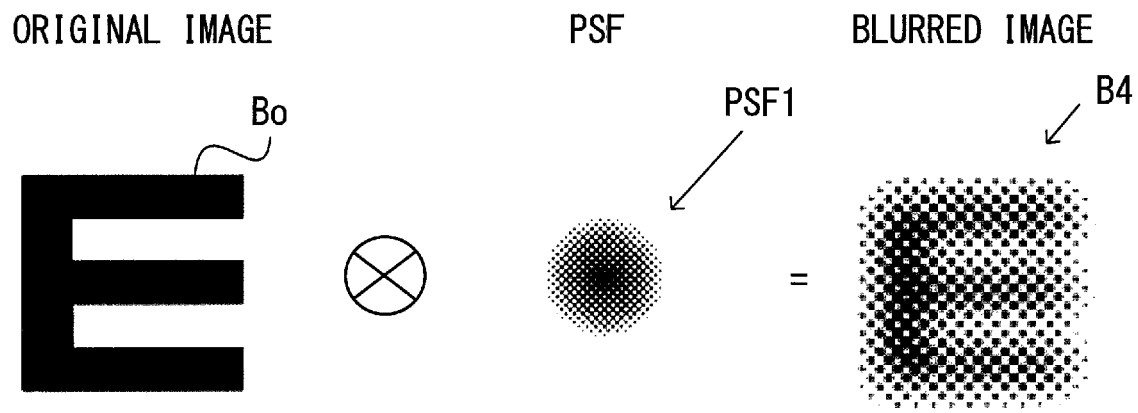
FIG. 15A is a conceptual figure for explanation of method for creating a blurred image and shows a case in which the blurring has no directional dependence.
Figure 15B:
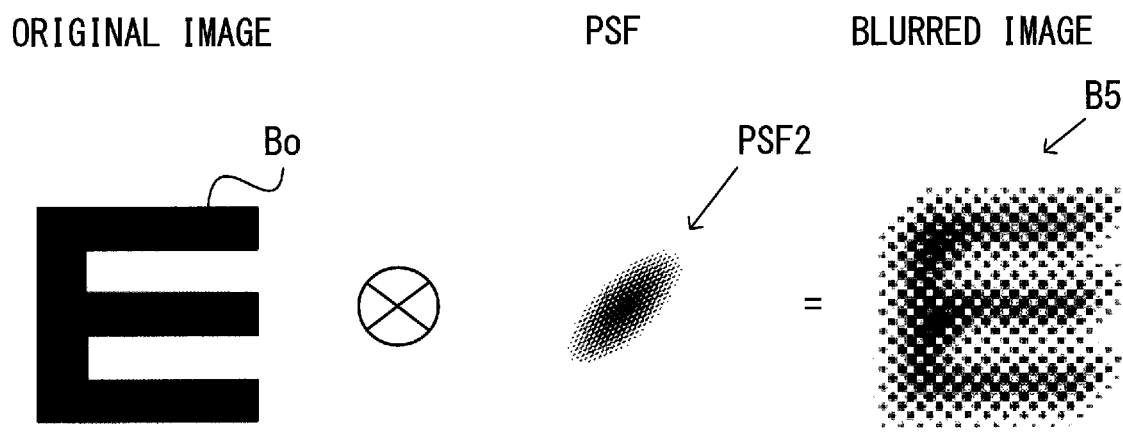
FIG. 15B is a conceptual figure for explanation of method for creating a blurred image and shows a case in which the blurring is directionally dependent.

FIGS. 15A and 15B are conceptual figures for explanation of methods for creating blurred images. FIG. 15A is a conceptual figure showing image processing when creating a blurred image B4 in which the blurring has no directional dependence. In this case, the blurred image B4 is created based upon a refractive power error when there is no astigmatism.

The blurred image B4 may be acquired by convolving the pixel values of the pixels in the image by employing a point spread function (PSF) as a kernel. The symbol with an X in a circle indicates convolution integral. When the original image Bo is convolved with a point spread function PSF1 having no directional dependence, an image is obtained in which each point is uniformly blurred, as shown by the blurred image B4. Thus, this blurred image B4 is a non-directionally dependent blurred image B4.

On the other hand, FIG. 15B is a conceptual figure showing image processing when creating a blurred image B5 in which the blurring is directionally dependent. In this case, the blurred image B5 is one that simulates blurring due to both astigmatism and also refractive power error.

When the original image Bo is convolved with a point spread function PSF2 having directional dependence (at a slanting direction of 45°), a blurred image is obtained in which each point is more strongly blurred in a slanting direction, as shown by the blurred image B5. In the following, this blurred image B5 is termed the "directionally dependent blurred image" B5, as appropriate. It would be possible to determine the directional dependence of this directionally dependent blurred image B5 on the basis of a direction of the astigmatic axis of the wearer.

It should be noted that the method for creating the blurred image B is not particularly limited; for example, the blurred image B reflected on the retina may be built up by calculation, using a ray tracing method for a system consisting of the object, the eyeglass lens, and the ocular optical system.

The original image Bo may be an image of any type. For example, it may be an image of an object which the subject sees on a daily basis, such as a landscape, a portable telephone, a book, a newspaper, a personal computer, a tablet terminal, a musical score, or the like.

The display control unit 511 (refer to FIG. 3) displays a plurality of blurred images B each having a different range of blurring upon the display screen 501 while changing over between them. The subject views this plurality of blurred images B having different blurring, and responds with impressions caused by viewing the blurred images B, such as whether they can be viewed comfortably, whether they are acceptable on a daily basis, or the like. And, on the basis of these responses, the sensitivity of the subject to blurring, and in particular to the range of blurring, can be evaluated and can be represented by a numerical value or by a grade.

It should be noted that a plurality of the blurred images B may be constructed as a moving image (i.e. a video).

Figure 16:
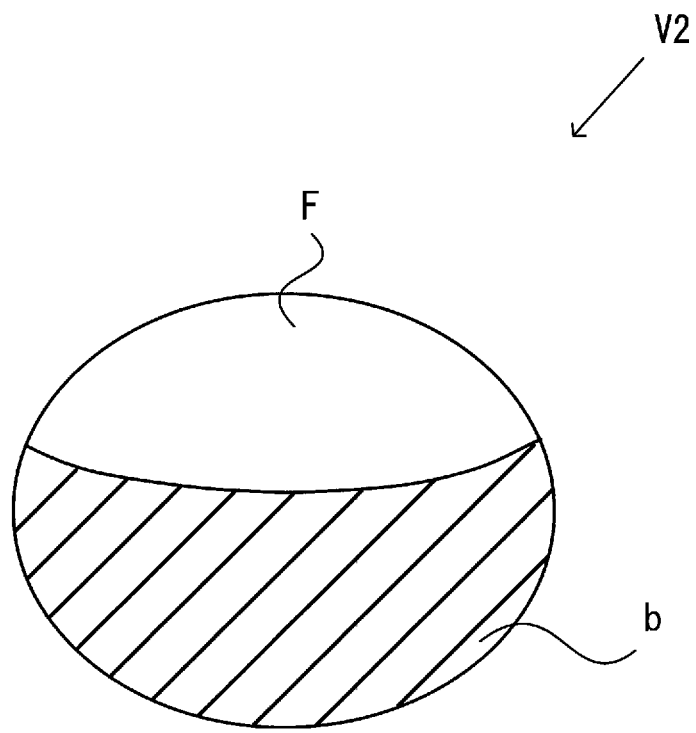
FIG. 16 is a conceptual figure for explanation of an example of a display image.

FIG. 16 is a figure for explanation of the range in the blurred image B where blurring is present. This field of view corresponding diagram V2 schematically shows a position of blurring b in the blurred image B within an outline of the eyeglass lens. In the left eye image 501L and the right eye image 501R, the display control unit 511 displays blurred images B having blurring at positions that, when the subject is wearing progressive power lenses, correspond to regions other than the distance area F, in other words having blurring at regions that correspond to the intermediate area, to the near area, to the side portions, and so on. The blurring level in the region corresponding to the distance area F is lower than in the other regions, or the region corresponding to the distance area F is not blurred.

In the example shown in FIG. 16 it is supposed that, during viewing at long distance, the sensitivity to blurring of a subject who is a wearer of a progressive power lens is measured in portions of his/her field of view other than those corresponding to the distance area F of the progressive power lens. Among wearers of eyeglass lenses, there are individuals who are sensitive to blurring generated in parts other than the portion through which they are directing their vision, there are individuals who are not so sensitive, and thus there are differences between individual persons. The information obtained by blurring sensitivity testing in which blurred images B explained with reference to FIG. 16 are presented to the wearer takes into account differences of this type between individual persons, and is used as appropriate when setting a target aberration distribution and/or a target power distribution for a progressive power lens.

In a similar manner the display control unit 511 can be configured to, for both the left eye image 501L and the right eye image 501R, to display blurred images B having blurring at positions that, when the subject is wearing progressive power lenses, correspond to regions other than the intermediate area, in other words having blurring at regions that correspond to the distance area, to the near area, to the side portions, and so on. In this case, the blurring level in the regions corresponding to the intermediate area is lower than in the other regions, or the region corresponding to the intermediate area is not blurred.

And, in a similar manner the display control unit 511 can be configured to, for both the left eye image 501L and the right eye image 501R, to display blurred images B having blurring at positions that, when the subject is wearing progressive power lenses, correspond to regions other than the near area, in other words having blurring at regions that correspond to the distance area, to the intermediate area, to the side portions, and so on. In this case, the blurring level in the regions corresponding to the near area is lower than in the other regions, or the region corresponding to the near area is not blurred.

Figure 17A:
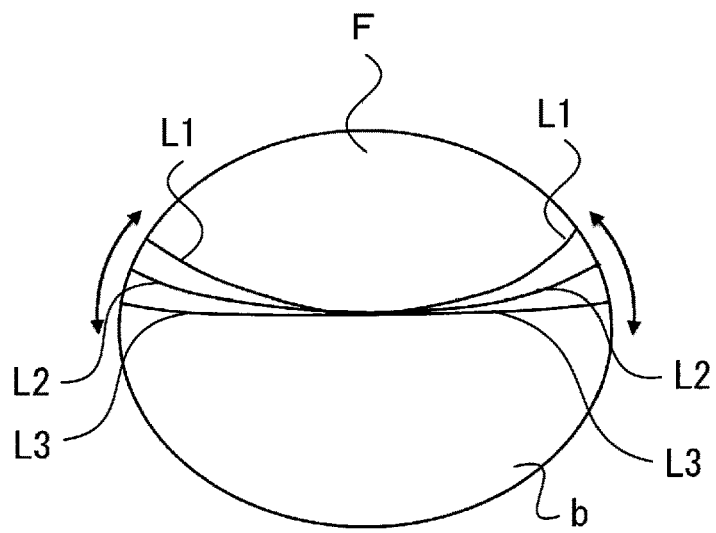
FIG. 17A is a conceptual figure showing an example in which ranges of blurring of display images are varied and is a conceptual figure for explanation of an example of a display image relating to a design of a distance area.
Figure 17B:
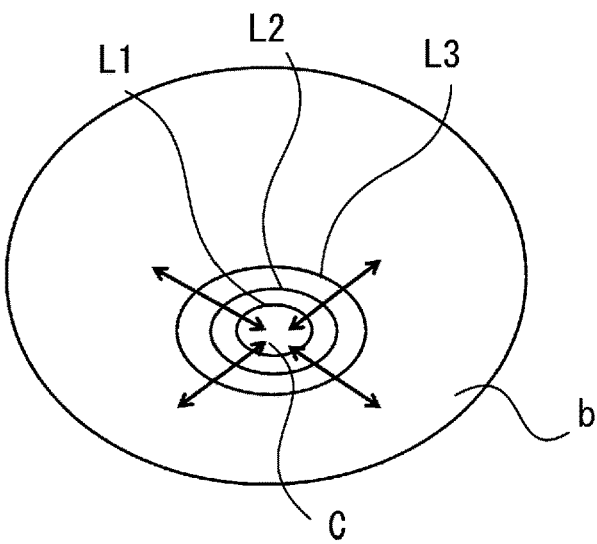
FIG. 17B is a conceptual figure showing an example in which ranges of blurring of display images are varied and is a conceptual figure for explanation of an example of a display image relating to a design of an intermediate area.
Figure 17C:
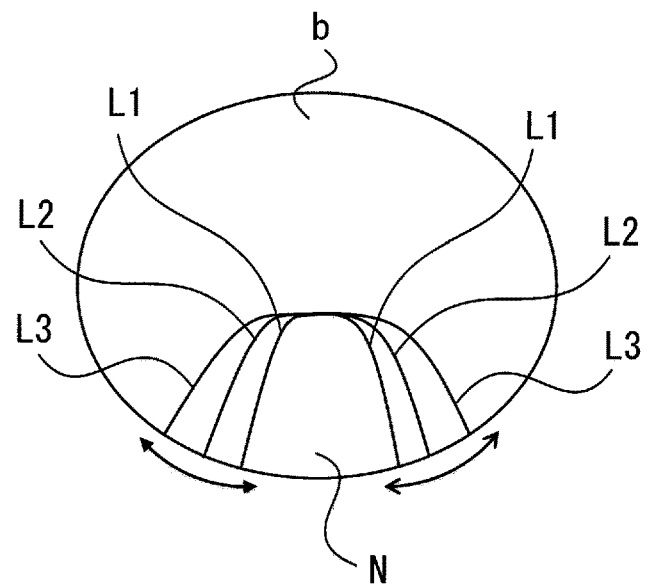
FIG. 17C is a conceptual figure showing an example in which ranges of blurring of display images are varied and is a conceptual figure for explanation of an example of a display image relating to a design of a near area.

FIGS. 17A, 17B and 17C are figures for explanation of how sensitivity to the range of blurring in the field of view of the subject is measured, for both the left eye image 501L and the right eye image 501R, by displaying a plurality of blurred images B having different ranges of blurring. Each of the plurality of blurred images B includes a plurality of regions whose blurring levels are mutually different.

FIG. 17A is a figure schematically showing three overlapped examples of blurred images B whose ranges of blurring in the distance area F or in areas surrounding it are different. Each of these three blurred images B includes a region having blurring b (hereinafter termed a "blurred region") in the near area, in other words in the lower portion of the eyeglass lens, and a region in the distance area, in other words in the upper portion of the eyeglass lens, in which the blurring level is less than that of the blurring b or which is not blurred (hereinafter termed a "non-blurred region"). In all three of the blurred images B, the blurred region is disposed lower than the non-blurred region. The boundaries in the three blurred images B between their blurred regions and their non-blurred regions are determined by boundary lines L1, L2, and L3 respectively. The example of FIG. 17A may be employed when evaluating the sensitivity to blurring in directions other than the direction in which the subject is directing his/her vision when viewing an object at a long distance.

FIG. 17B is a figure schematically showing three overlapped examples of blurred images B whose ranges of blurring in the intermediate area C or in areas surrounding it are different. Each of these three blurred images B includes a blurred region outside the intermediate area C of the eyeglass lens, in other words at peripheral portions or the like of the eyeglass lens, and a non-blurred region in the intermediate area C. In the three blurred images B, the non-blurred region is arranged to surround the blurred region. The boundaries in the three blurred images B between the blurred regions and the non-blurred regions are determined by boundary lines L1, L2, and L3 respectively. The example of FIG. 17B may be employed when evaluating the sensitivity to blurring in directions other than the direction in which the subject is directing his/her vision when viewing an object at an intermediate distance.

And FIG. 17C is a figure schematically showing three overlapped examples of blurred images B whose ranges of blurring in the near area N or in areas surrounding it are different. Each of these three blurred images B includes a blurred region toward the distance area, in other words in the upper portion of the eyeglass lens, and a non-blurred region toward the near area, in other words in the lower portion of the eyeglass lens. In all three of the blurred images B, the blurred region is arranged to be above the non-blurred region. The boundaries in the three blurred images B between the blurred regions and the non-blurred regions are determined by boundary lines L1, L2, and L3 respectively. The example of FIG. 17C may be employed when evaluating the sensitivity of to blurring in directions other than the direction in which the subject is directing his/her vision when viewing an object at a short distance.

It should be understood that the number of blurred images B having different ranges of blurring displayed to the subject is not limited to being three, as in the case of FIGS. 17A, 17B, and 17C described above; there could be any suitable number thereof. Furthermore, the non-blurred regions are not limited to being the distance area, the intermediate area, and the near area; they could be set to any desired positions and ranges upon the eyeglass lens as appropriate, so as to match directions in which the wearer of an eyeglass lens to be designed often looks on a daily basis, or the like.

With the method for designing an eyeglass lens of the present embodiment, it is possible to set a target aberration distribution and/or a target power distribution, or a value of the upper permitted limit of aberration at one or a plurality of points of the eyeglass lens that is being designed, on the basis of the information that has been obtained by blurring sensitivity testing, and the information is related to the sensitivity to blurring, particularly the range of blurring, of the subject or, in other words, a wearer of the eyeglass lens being designed. In particular, it is preferable to set the target aberration and the value of the upper limit for permitted aberration for astigmatism.

The information obtained by blurring sensitivity testing in which the blurred images B explained with reference to FIG. 17A, 17B or 17C are presented to the wearer, is preferably employed for setting, for example, the width in the horizontal direction (refer to FIG. 12) where the target aberration becomes less than or equal to a predetermined value at a predetermined height on the distance area, the intermediate area, or the near area of the progressive power lens, or the like.

It should be understood that, in the blurred images B, for example, it would also be acceptable to vary the blurring level continuously by simulating the side portions of a progressive power lens or the like.

The eyeglass lens ordering and order receiving system in relation to design of eyeglass lens will now be explained. The eyeglass lens ordering and order receiving system according to the present embodiment is capable of supplying an eyeglass lens in which the optical characteristics such as aberration are set in an appropriate manner according to the sensitivity of the wearer to blurring in his/her field of view, as described above. The configuration of the eyeglass lens ordering and order receiving system according to the present embodiment is similar to the configuration of the eyeglass lens ordering and order receiving system according to the embodiment described above (refer to FIG. 7).

The fundamental flow of the procedure for supplying an eyeglass lens is the same as that of the procedure for supplying an eyeglass lens in the embodiment described above (refer to FIG. 8). However, since the details of steps S11 and S22 and of the order information inputted in step S12 are different from those in the flow chart shown in FIG. 8, these features will be described below.

Figure 18:
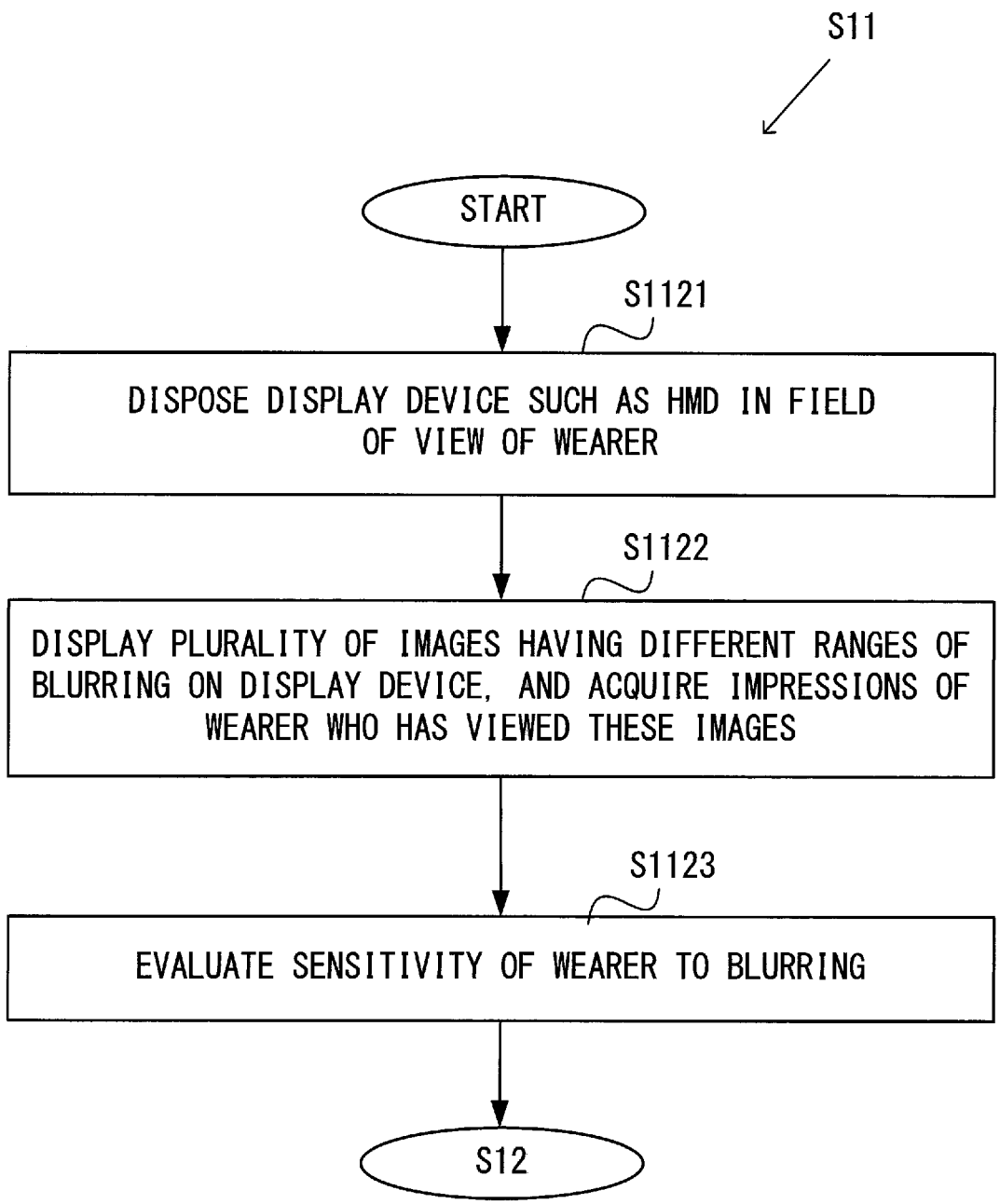
FIG. 18 is a flow chart showing flow of a method for designing an eyeglass lens according to an embodiment.

FIG. 18 is a flow chart showing the flow of the step S11 (refer to FIG. 8) in the present embodiment. In the present embodiment the ordering entity, which is a shop that sells eyeglass lenses or personnel thereof, performs blurring sensitivity testing with a wearer as a subject, and thereby acquires information relating to the sensitivity of that wearer to blurring.

In a step S1121, the ordering entity causes the wearer to put on the display device 50 such as an HMD or the like, and disposes the display screen 501 in the field of view of the wearer. When the step S1121 has been completed, a step S1122 is started.

In the step S1122, the ordering entity sequentially displays a plurality of blurred images B having different ranges of blurring upon the display screen 501, thus causing the wearer to view those images, and acquires the impressions received by the wearer who has viewed these blurred images B. For example, as shown in FIG. 17A, the ordering entity may cause the wearer to view the blurred images B in which the boundary lines are denoted by L3, L2, and L1 between their blurred regions and their non-blurred regions in this order. When the wearer has viewed each of these blurred images B, the ordering entity receives and records whether or not the wearer is able to accept that blurred image B. And, when the step S1122 has been completed, a step S1123 is started.

It should be understood that the order in which the blurred images B having different blurring levels are presented is not particularly limited. Blurred images B whose ranges of blurring are sufficiently small to be acceptable to the wearer can be presented once in every few images, so that the wearer does not become habituated to the blurring.

In the step S1123, the ordering entity evaluates the sensitivity of the wearer who has viewed the blurred images B to blurring, particularly the range of blurring in his/her field of view. On the basis of the responses from the wearer who has thus viewed the blurred images received in the step S1122, the ordering entity converts the sensitivity of the wearer to blurring into a numerical value according to a predetermined standard, and records that value. For example, suppose that the wearer has viewed the blurred images B explained with reference to FIG. 17A, as described above. If the wearer has responded that the blurred image B having the boundary line L2 is acceptable but that the blurred image B having the boundary line L1 is not acceptable, then L2 or, numerals or symbols or the like corresponding to L2 is acquired as a parameter (a blurring sensitivity parameter) that indicates the sensitivity of the wearer to blurring or to the range of blurring. When the step S1123 has been completed, a step S12 (refer to FIG. 8) is started.

In the step S12, the ordering entity determines order information for the eyeglass lens, including information relating to sensitivity of the wearer to blurring, particularly the range of blurring, in his/her field of view, such as the blurring sensitivity parameter acquired in the step S1123. And the ordering entity causes the display unit 14 of the ordering device 1 to display an ordering screen, and inputs order information via the input unit 15.

FIG. 19 is a figure showing an example of the ordering screen. The ordering screen 100b of the present embodiment has a structure similar to that of the ordering screen 100a of the embodiment described above, but the sensitivity information item (106b) is different from that on the ordering screen of the embodiment described above. In this sensitivity information item 106b, for blurring sensitivity testing, numerical values such as a blurring sensitivity parameter or the like is inputted that specify the intensity of sensitivity of the wearer to blurring, and in particular to the range of blurring.

In the example of FIG. 19, the intensity of sensitivity to the range of blurring is shown by numerical values in three stages ("3" for the distance area F, "2" for the intermediate area C, and so on) in the case of viewing through the distance area F (refer to FIG. 17A), in the case of viewing through the intermediate area C (refer to FIG. 17B), and in the case of viewing through the near area N (refer to FIG. 17C). In the example of FIG. 19, the numerals 1, 2, and 3 correspond to the boundary lines L1, L2, and L3 of FIGS. 17A, 17B, and 17C, and the blurred images B corresponding to those boundary lines indicate the tolerance limits of the wearer when the range of blurring is progressively widened.

It should be understood that the way in which the sensitivity to blurring, or to the range of blurring, is expressed is not particularly limited to the method described above, as long as that sensitivity can be expressed and transmitted according to a predetermined standard.

As well as, or instead of, numerical values that specify the intensity of the sensitivity of the wearer to blurring, the ordering screen 100b may also be adapted to input a design parameter, such as an index that indicates a range where astigmatism of the eyeglass lens to be designed is small, or the like. As an index indicating a range where astigmatism of the eyeglass lens is small, for example, in a progressive power lens, as shown by the broken lines or the single dotted chain lines in FIG. 12, a length or the like where the astigmatism is less than or equal to a predetermined value may be set in the horizontal direction at a predetermined height in the distance area or in the near area. The design parameter may be determined on the basis of a position of the boundary line for toleration by the wearer between the blurred region and the non-blurred region, or the like.

Next, the feature will be explained that, in a step S22 (refer to FIG. 8), the design unit 212 of the order receiving device 2 (refer to FIG. 3) performs design of the eyeglass lens on the basis of the order information that has been received (refer to the ordering screen 100b).

FIG. 20 is a flow chart showing the procedure for designing the eyeglass lens corresponding to the step S22. In a step S2221, the order receiving device 2 acquires the prescription data for the eyeglass lens and, the information relating to the sensitivity of the wearer to blurring, and in particular to the range of blurring, and/or a design parameter such as the index described above that indicates the range where the astigmatism is small, and so on. And the order receiving device 2 also acquires a fitting parameter such as a pantoscopic angle, a warp angle, a vertex distance, or the like. When the step S2221 has been completed, a step S2222 is started.

In the step S2222, the design unit 212 of the order receiving device 2 sets the target aberration distribution and/or the target power distribution for the eyeglass lens on the basis of the information acquired in the step S2221 in relation to the sensitivity of the wearer to blurring, in particular to the range of blurring, and/or the design parameter acquired in the step S2221.

Figure 21:
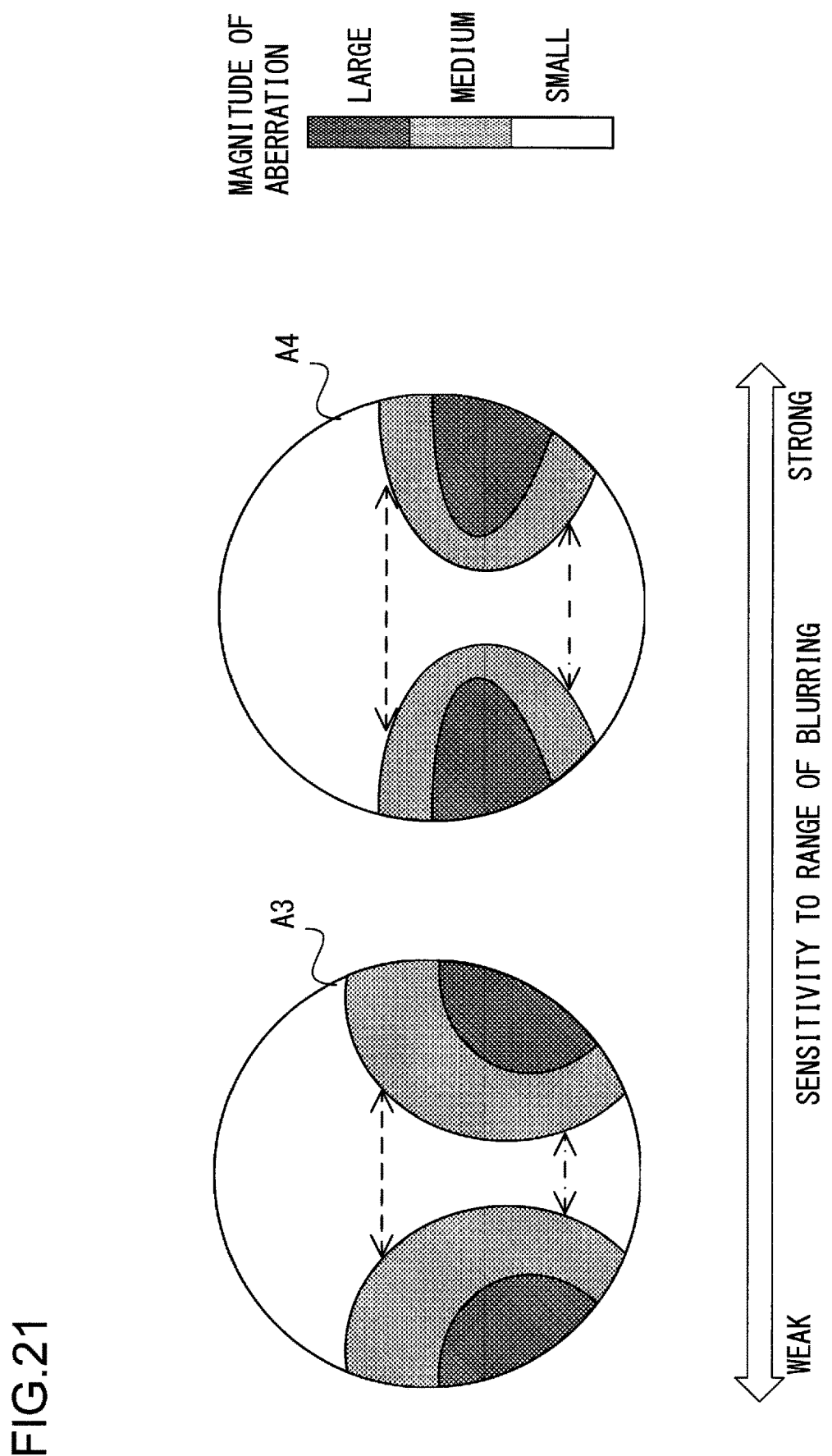
FIG. 21 is a figure schematically showing distributions of aberration upon an eyeglass lens being designed.

FIG. 21 is a conceptual figure showing an example of setting target aberration on the basis of the sensitivity of the wearer to the range of blurring. Two aberration distribution diagrams are shown in the center of the figure, and a portion of the figure on the rightmost side shows the magnitude of aberration corresponding to the pattern employed for representing the magnitude of aberration in the aberration distribution diagrams. The definitions of the broken line arrow signs and the single dotted chain line arrow signs are the same as in the case of FIG. 12.

In the aberration distribution diagrams shown in FIG. 21, the aberration distribution diagram A3 on the left side shows a lens for a wearer whose sensitivity to the range of blurring is weak. With a lens of this sort, although the range where astigmatism is small is narrow, level of blur in an image is small since change of astigmatism is small. On the other hand, the aberration distribution diagram A4 on the right side shows a lens for a wearer whose sensitivity to the range of blurring is stronger than in the case of the aberration distribution diagram A3. With a lens of this sort, although change in degree of blur is large, the ranges where astigmatism is small in the distance area and in the near area are designed to be wider than in the case of the aberration distribution diagram A3. When the step S2222 has been completed, a step S2223 is started.

In the step S2223 (refer to FIG. 20), the order receiving device 2 determines the overall shape of the eyeglass lens on the basis of the target aberration distribution and/or the target power distribution that have been set. When the step S2223 has been completed, a step S2224 is started. In the step S2224, the order receiving device 2 makes a decision as to whether the optical characteristics of the eyeglass lens, such as its refractive power and its astigmatism and so on, satisfy a desired condition. If the desired condition is satisfied, then an affirmative decision is reached in the step S2224, and the design processing terminates and the step S23 (refer to FIG. 8) is started. Such a desired condition is a condition that satisfies all the items of the prescription while reflecting the sensitivity of the wearer. However, if the desired condition is not satisfied, then a negative decision is reached in the step S2224, and the step S2223 is started.

According to the second embodiment as described above, in addition to the beneficial operational effects obtained with the first embodiment, the following further beneficial operational effects are obtained.

(1) In the method for designing an eyeglass lens of the present embodiment, in the display of the image upon the display device 50, a plurality of blurred images B are displayed, each having a different range of blurring b, and in evaluation of the sensitivity, the sensitivity of the subject to blurring is evaluated on the basis of the impressions of the subject who has viewed the plurality of images B. Due to this, it is possible to design an eyeglass lens that is matched to the wearer, on the basis of the sensitivity of the wearer to the range of blurring and so on.

(2) In the method for designing an eyeglass lens of the present embodiment, each of the blurred images B include a plurality of regions whose blurring levels are mutually different, and/or blurring whose blurring level changes continuously. Due to this, it is possible to measure the sensitivity of the wearer to blurring in a more accurate manner, while performing matching to the type of eyeglass lens to be designed and to various situations.

(3) In the method for designing an eyeglass lens of the present embodiment, in the display of the image upon the display device 50, a region whose blurring level is relatively large is displayed so as to be disposed below a region whose blurring level is relatively small or a region where there is no blurring, and, in evaluation of the sensitivity, the sensitivity to blurring when the subject is looking at an object at a long distance is evaluated. Due to this, it is possible to design an eyeglass lens such as a progressive power lens or the like that is matched to the wearer, on the basis of the sensitivity to blurring when looking at a long distance.

(4) In the method for designing an eyeglass lens of the present embodiment, in the display of the image upon the display device 50, a region whose level is relatively large is displayed so as to be disposed above a region whose blurring level is relatively small or a region where there is no blurring; and, in evaluation of the sensitivity, the sensitivity to blurring when the subject is looking at an object at a short distance is evaluated. Due to this, it is possible to design an eyeglass lens such as a progressive power lens or the like that is matched to the wearer, on the basis of the sensitivity to blurring when looking at a short distance.

(5) In the method for designing an eyeglass lens of the present embodiment, in the display of the image upon the display device 50, a region whose blurring level is relatively small or a region where there is no blurring is displayed so as to be disposed surrounded by a region whose blurring level is relatively large; and, in evaluation of the sensitivity, the sensitivity to blurring when the subject is looking at an object at an intermediate distance is evaluated. Due to this, it is possible to design an eyeglass lens such as a progressive power lens or the like that is matched to the wearer, on the basis of the sensitivity to blurring when looking at an intermediate distance.

The following variations also come within the range of the present invention, and can also be combined with the embodiment described above.

Variant Embodiment 1

In the embodiment described above, an example was explained in which a plurality of blurred images B having different ranges of blurring were displayed upon the display device 50, but it would also be possible to provide a configuration in which a plurality of blurred images B having different blurring levels are displayed upon the display device 50. For example, it would be possible to display a plurality of different blurred images B upon the display device 50 while keeping the blurring level fixed at one level, and subsequently to change the blurring level and then to keep it fixed at another different level while further displaying a plurality of different blurred images B upon the display device 50. By doing this, it would be possible to measure the sensitivity of the wearer to the range of blurring b in a more precise manner, since the sensitivity would be measured with different blurring levels.

It should be understood that it would be possible to set a plurality of blurred images B in an appropriate manner by keeping their ranges of blurring fixed while changing their blurring levels, or the like.

Variant Embodiment 2

While, in the embodiment described above, it was arranged for the blurring level to change at the boundary lines L1, L2, and L3 between the blurred regions and the non-blurred regions, it would also be possible to arrange for the blurring level to change stepwise, or continuously, between the blurred regions and the non-blurred regions, in other words at the edges of the blurred regions.

Figure 22:
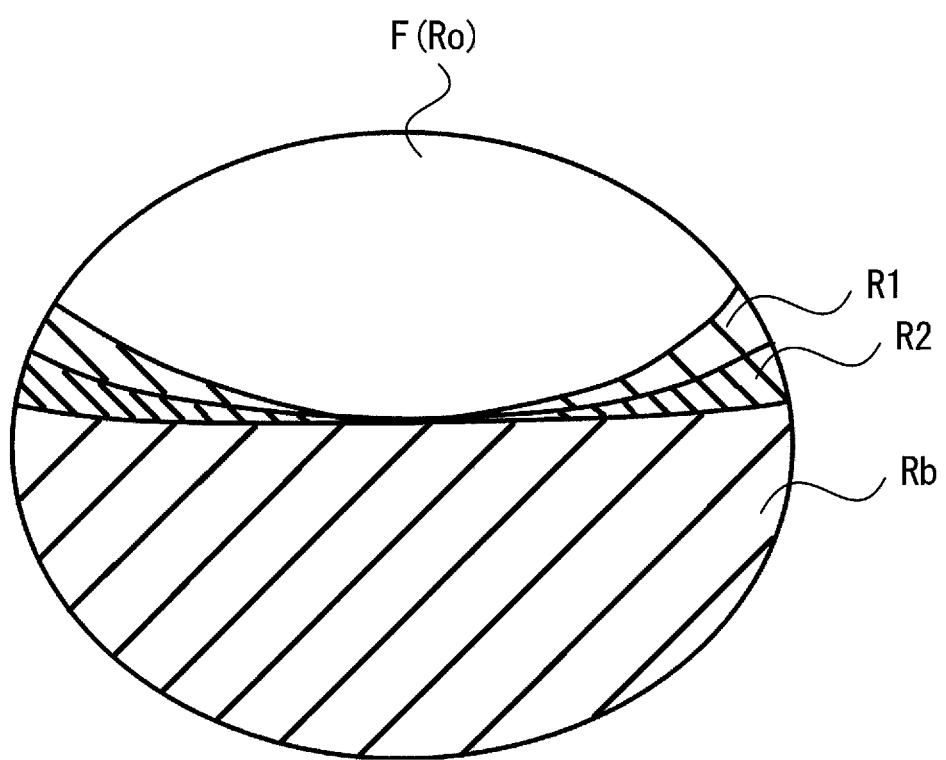
FIG. 22 is a conceptual figure for explanation of an example of a display image.

FIG. 22 is a field of view corresponding figure, schematically showing a blurred image B in which the blurring level changes stepwise at the boundary between a blurred region Rb and a non-blurred region Ro. The blurring level becomes higher in the following order: the non-blurred region Ro, a first intermediate region R1, a second intermediate region R2, and the blurred region Rb. By changing the blurring level stepwise in this manner at the boundary between the blurred region Ro and the non-blurred region Rb, or by changing it continuously, it is possible to display a blurred image B that simulates the manner of blurring by a progressive power lens or the like, and it is possible to measure the sensitivity of the wearer to blurring in a more accurate manner in a situation that is close to when actually wearing an eyeglass lens.

The Third Embodiment

The display device 50 and the eyeglass lens ordering and order receiving system 10 according to the third embodiment have configurations similar to those of the display device 50 and the eyeglass lens ordering and order receiving system 10 according to the first embodiment, but the display device 50 differs from the first embodiment in the feature that, in a part of the field of view of the subject, it displays a plurality of images whose positions are different (hereinafter termed "test images") while changing them over. Elements that are the same as elements of the first embodiment will be referred to by the same reference symbols as in the first embodiment, and explanation thereof will be omitted, depending upon each case.

With this method for designing an eyeglass lens according to the third embodiment: a subject who is also a wearer of the eyeglass lens to be designed is caused to view test images that are at different positions; information is acquired in which sensitivity to line of sight direction at a distance that is determined in advance, such as at a short distance or at an intermediate distance is evaluated; and the eyeglass lens is designed on the basis of that information. In the following, this testing for evaluating the sensitivity of the subject to his/her line of sight direction will be termed "line of sight direction sensitivity testing". Moreover, in the following, explanation will principally be based upon measuring the sensitivity to the line of sight at a short distance and at an intermediate distance, but it would also be acceptable to measure the sensitivity to the line of sight at a long distance.

The test images that are employed in the present embodiment are not particularly limited, but, when measuring the sensitivity of the subject to the direction of the line of sight at a predetermined distance, the test images can be images of an object or the like that the subject sees at that distance on a daily basis.

When measuring the sensitivity of the subject to the direction of the line of sight at a short distance, as the image of an object that the subject sees at a short distance on a daily basis, the test image may be at least one selected from a portable telephone, a book, a newspaper, a magazine, and the like. And, when measuring the sensitivity of the subject to the direction of the line of sight at an intermediate distance, as the image of an object that the subject sees at an intermediate distance on a daily basis, the test image may be at least one selected from a personal computer, a tablet terminal, a musical score, and the like.

The display control unit 511 (refer to FIG. 3) displays a plurality of display images upon the display screen 501 in which the test image is disposed in different positions, such as in the near area or in the intermediate area, while changing over between them. The subject views this plurality of different display images displayed upon the display screen 501, and responds with his/her impressions caused by viewing these display images, such as whether they can be viewed comfortably, whether they are acceptable on a daily basis, in which position the test images can most easily be viewed when they are displayed, and so on. And, on the basis of these responses, the sensitivity of the subject to the direction of the line of sight is evaluated and can be represented by a numerical value or by a grade.

It should be noted that a plurality of the display images may be configured as a moving image.

Figure 23:
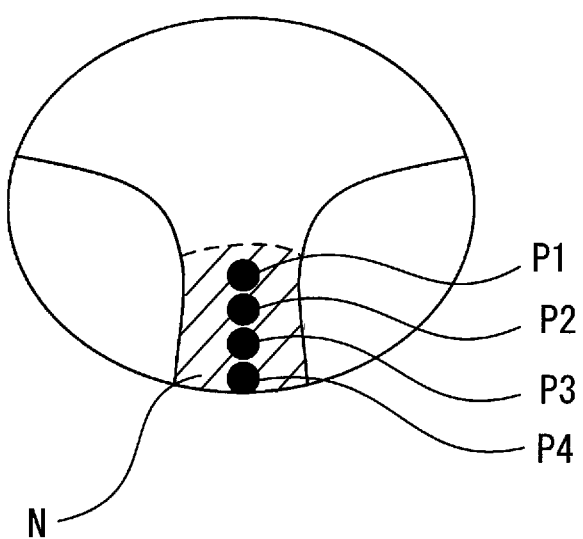
FIG. 23 is a conceptual figure for explanation of display positions of display images.

FIG. 23 is field of view corresponding figures, showing positions at which test images may be disposed in display images. Test images are displayed at a plurality of positions P1, P2, P3, and P4 at different heights in a near area N of a progressive power lens. Due to this, it is possible to evaluate the sensitivity of the subject to the height of his/her line of sight, including preference or comfort for the amount of eye dropping when the subject is viewing an object at a short distance, or the like.

FIGS. 24A, 24B, 24C and 24D are figures schematically showing an example of display images in which test images T are disposed at the positions P1 (FIG. 24A), P2 (FIG. 24B), P3 (FIG. 24C), and P4 (FIG. 24D) of FIG. 23 in the near area N. In the example of FIGS. 24A, 24B, 24C and 24D, images of a smartphone are employed as the test images. In this figure, outlines of the progressive power lens and of its side portions are shown. However, these particular outlines are not specifically required on the condition that the test images T are shown at positions upon the display screen 501 that correspond to the positions P1 through P4 of the near area of the eyeglass lens.

By receiving responses from the subject after causing the subject to view the plurality of display images explained in connection with FIGS. 24A through 24D, it is also possible to acquire information about what position an object such as a smartphone or the like is disposed at in the field of view of the subject when the subject is usually looking at the object. And, due to this, it becomes possible to design eyeglass lenses that make it possible to see objects more easily.

It should be understood that the number of display images including test images T at different positions that are displayed to the subject is not limited to being four as shown in FIGS. 24A, 24B, 24C and 24D described above; this could be any number.

With the method for designing an eyeglass lens of the present embodiment, it is possible to set a target aberration distribution, and/or a target power distribution, or a value of the upper permitted limit of aberration at one or a plurality of points upon the eyeglass lens being designed, on the basis of information that has been obtained by line of sight direction sensitivity testing, and the information is related to the sensitivity to the direction of the line of sight, particularly the height of the line of sight of the subject or, in other words, a wearer of the eyeglass lens being designed. In particular, it is preferable to set the target aberration and the value of the upper permitted limit of aberration for astigmatism.

The eyeglass lens ordering and order receiving system relating to design of the eyeglass lens will now be explained. The eyeglass lens ordering and order receiving system according to the present embodiment is capable of providing an eyeglass lens for which the optical characteristics such as aberration and so on have been set in an appropriate manner on the basis of the sensitivity of the wearer to the direction of his/her line of sight, as described above. The configuration of the eyeglass lens ordering and order receiving system according to the present embodiment is similar to the structure of the eyeglass lens ordering and order receiving system 10 according to the embodiment described above (refer to FIG. 7).

The fundamental flow of the procedure for supplying an eyeglass lens is the same as that of the procedure for supplying an eyeglass lens in the embodiment described above (refer to FIG. 8). However, since the details of the steps S11 and S22 and the order information inputted in the step S12 are different from those in the flow chart shown in FIG. 8, these features will be described below.

Figure 25:
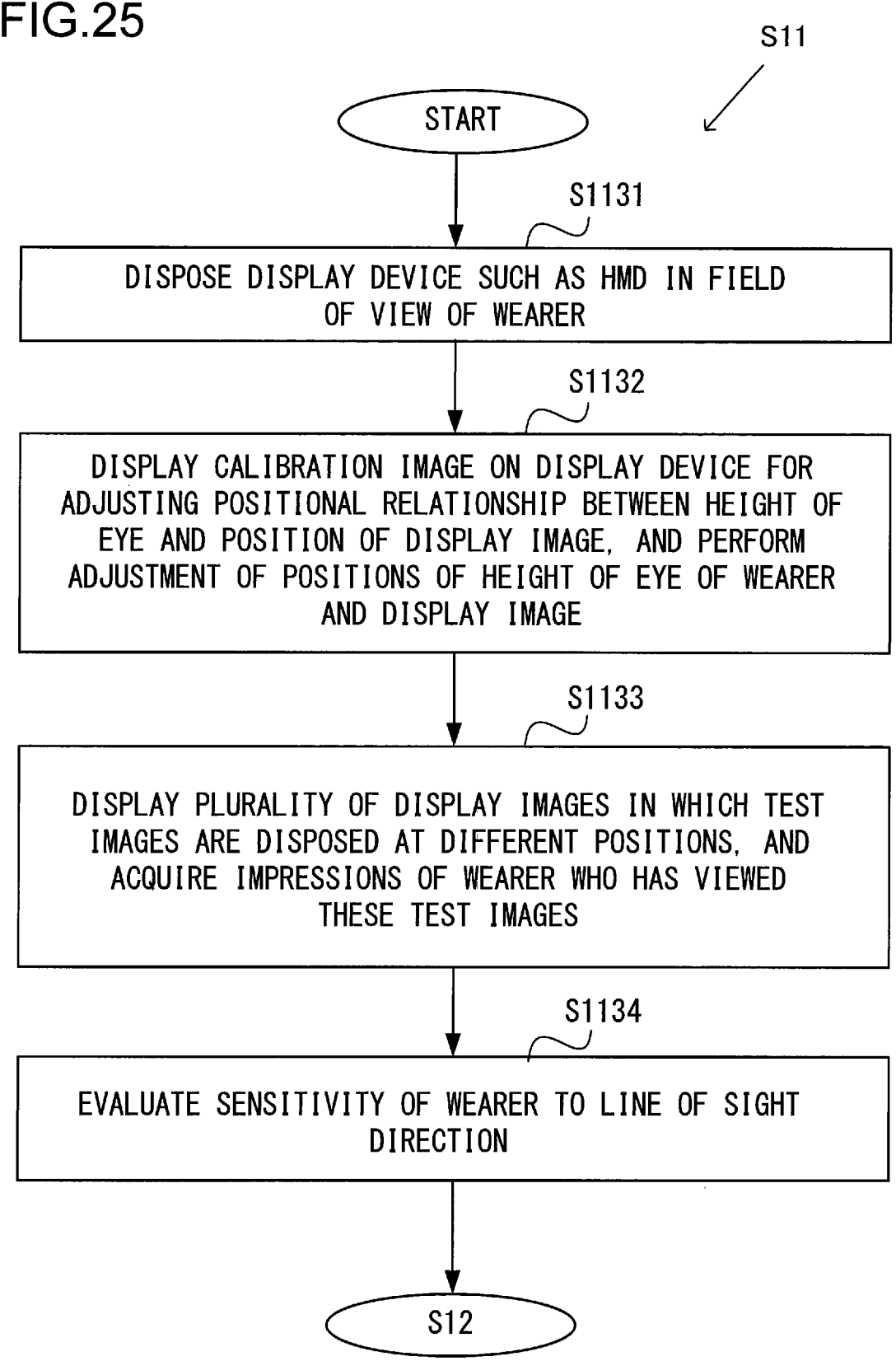
FIG. 25 is a flow chart showing flow of a method for designing an eyeglass lens according to an embodiment.

FIG. 25 is a flow chart showing the flow of a step S11 (refer to FIG. 8) in the present embodiment. In the present embodiment the ordering entity, which is the shop that sells the eyeglass lens or the personnel thereof, performs line of sight direction sensitivity testing upon a wearer as a subject, and thereby acquires the information relating to the sensitivity of the wearer to the direction of his/her line of sight.

In a step S1131, the ordering entity causes the wearer to put on the display device 50 such as an HMD or the like, and disposes the display screen 501 in the field of view of the wearer. When the step S1131 has been completed, a step S1132 is started.

In the step S1132, a calibration image for adjusting the positional relationship between the height of the eye of the subject and the position of the display image is displayed upon the display device 50, and adjustment of the positions of the eye of the subject and of the display image is performed. The display device 50 displays marks at positions corresponding to fitting points in the left eye image 501L and the right eye image 501R, so that, when the wearer looks straight ahead, those marks become positions through which the lines of sight of the wearer pass, and the wearer may adjust the position in which he wears the HMD.

Then, in the step S1133, the ordering entity displays a plurality of display images in which test images T are disposed in different positions, and acquires the impressions of the wearer who has viewed these test images T. For example, the ordering entity may cause the wearer to view the display images explained with reference to FIGS. 24A, 24B, 24C, and 24D in that order. After the wearer has viewed all of the display images, or after the wearer has viewed each of the display images, the ordering entity receives and records the responses of the wearer as to the position of the test image T that the wearer could view most easily, or whether the display images were acceptable or not, or the like. And, when the step S1133 has been completed, a step S1134 is started.

It should be understood that the order in which the display images having test images T at different positions are presented is not particularly limited.

In the step S1134, the ordering entity evaluates the sensitivity of the wearer who has viewed the display images including the test images T to the line of sight direction in the field of view of the wearer, and in particular the sensitivity to the height of the line of sight. On the basis of the response from the wearer who has thus viewed the test images T obtained in the step S1133, the ordering entity converts the sensitivity of the wearer to the direction of his/her line of sight into a numerical value according to a predetermined standard, and records that value. For example, suppose that the wearer has viewed the plurality of display images explained with reference to FIGS. 24A, 24B, 24C and 24D, as described above. If the wearer has responded that the position P2 of the test image T explained in FIG. 24B is the easiest to see, then P2 or, a numeral or a symbol or the like corresponding to P2 is acquired as a parameter (a line of sight direction sensitivity parameter) that specifies the sensitivity of the wearer to the direction of his/her line of sight or to the height of his/her line of sight. When the step S1134 has been completed, a step S12 (refer to FIG. 8) is started.

In the step S12, the ordering entity determines order information for the eyeglass lens, including information relating to sensitivity of the wearer to the line of sight direction in his/her field of view, and in particular relating to the sensitivity to the height of his/her line of sight, such as the line of sight sensitivity parameter or the like acquired in the step S1134. And the ordering entity causes the display unit 14 of the ordering device 1 to display an ordering screen, and inputs order information via the input unit 15.

FIG. 26 is a figure showing an example of the ordering screen. The ordering screen 100c of the present embodiment has a configuration similar to that of the ordering screen 100a of the embodiment described above, but the sensitivity information item (106c) is different from that on the ordering screen of the embodiment described above. In this sensitivity information item 106c, for line of sight sensitivity testing, a numerical value such as a line of sight sensitivity parameter or the like is inputted that specify the intensity of the sensitivity of the wearer to the direction of his/her line of sight, and in particular to the height of his/her line of sight.

In the example of FIG. 26, for the near area and the intermediate area, the intensity of the sensitivity of the subject to the line of height is expressed by numerical values having four stages (for the near area the value is "2", and for the intermediate area the value is "3"). In the example of FIG. 26, the numerals 1, 2, 3, and 4 respectively correspond to the positions P1, P2, P3, and P4 where the test images T of FIG. 23 are arranged, and, when the position of the test image T was changed, the numeral indicates that it was easiest for the wearer to see when it was arranged in that position.

It should be understood that the way in which the sensitivity of the wearer to the direction of the line of sight, or to the height of the line of sight, is expressed is not particularly limited, as long as that sensitivity can be expressed and transmitted according to a predetermined standard.

Moreover, on the ordering screen 100c, in addition to or instead of the numerical values that indicate the sensitivity of the wearer to the direction of his/her line of sight, it would also be possible to provide a configuration with which, for the eyeglass lens that is being designed, a design parameter such as a coordinate of a position for reference in design or the like is inputted. For example, the position (P1, P2, P3, or P4) of the test image T when the wearer has responded that he can view it best may be taken as being the position for reference in design.

Next, the feature will be explained that, in the step S22 (refer to FIG. 8), the design unit 212 of the order receiving device 2 performs design of the eyeglass lens on the basis of the order information that has been received (refer to the ordering screen 100c).

FIG. 27 is a flow chart corresponding to the step S22, showing the procedure for designing the eyeglass lens. In a step S2231, the order receiving device 2 acquires the prescription data for the eyeglass lens and, the information relating to the sensitivity of the wearer to the direction of his/her line of sight, particularly to the height of his/her line of sight, and/or a design parameter, such as the coordinate of the position for reference in design described above or the like. And the order receiving device 2 also acquires a fitting parameter for an appropriate frame, such as a pantoscopic angle of a frame, a warp angle, the vertex distance, or the like. When the step S2231 has been completed, a step S2232 is started.

In the step S2232, the design unit 212 of the order receiving device 2 sets the target aberration distribution and/or the target power distribution for the eyeglass lens on the basis of the information acquired in the step S2231 relating to the sensitivity of the wearer to the direction of his/her line of sight, and in particular to the height of his/her line of sight, and/or the design parameter. The design unit 212 may, for example, set the target aberration distribution and/or the target power distribution so that the astigmatism at the coordinate of the position for reference in design specified by the design parameter becomes particularly small. When the step S2232 has been completed, a step S2233 is started.

In the step S2233, the order receiving device 2 determines the overall shape of the eyeglass lens on the basis of the target aberration distribution and/or the target power distribution that have been set. When the step S2233 has been completed, a step S2234 is started. In the step S2234, the order receiving device 2 makes a decision as to whether the optical characteristics of the eyeglass lens, such as its refractive power and its astigmatism and so on, satisfy a desired condition. If the desired condition is satisfied, then an affirmative decision is reached in the step S2234, and the design processing terminates and the step S23 (refer to FIG. 8) is started. However, if the desired condition is not satisfied, then a negative decision is reached in the step S2234, and the step S2233 is started.

According to the third embodiment as described above, in addition to the beneficial operational effects obtained with the first or second embodiment, the following further beneficial operational effects are also obtained.

(1) With the method for designing an eyeglass lens of the present embodiment, in the display of the image by the display device 50, a plurality of test images T whose positions in a portion of the field of view of the subject are different are displayed while changing over between the plurality of test images T; and, in evaluation of the sensitivity, the sensitivity of the subject to the direction of his/her line of sight at a distance that is determined in advance is evaluated on the basis of the impressions of the subject who has viewed the test images T. Due to this, it is possible to measure the sensitivity of the wearer in relation to the direction of his/her line of sight in an accurate manner by presenting images at a desired position while taking the eye of the wearer as reference, so that it is possible to design an eyeglass lens that is matched to the wearer on the basis of that sensitivity.

(2) In the method for designing an eyeglass lens of the present embodiment, in the display of the image by the display device 50, a plurality of the test images T may be displayed at different heights, and, in the evaluation of the sensitivity, the sensitivity of the subject to the height of his/her line of sight at the distance that is determined in advance may be evaluated on the basis of the impressions of the subject who has viewed the test images T. Due to this, it is possible to measure the sensitivity of the wearer in relation to the height of his/her line of sight in an accurate manner, so that it is possible to design an eyeglass lens that is matched to the wearer on the basis of that sensitivity.

(3) In the method for designing an eyeglass lens of the present embodiment, in a region corresponding to any one region selected from among a distance area of a progressive power lens, a near area thereof, and an intermediate area thereof between the distance area and the near area, a plurality of test images T at different positions are displayed while changing over between the plurality of the test images T, and the sensitivity of the subject to the direction of his/her line of sight at the distance seen through the one region that has been selected may be evaluated. Due to this, in relation to each of a long distance, a short distance, and an intermediate distance, it is possible to measure the sensitivity of the wearer in relation to the direction of his/her line of sight in an accurate manner, so that it is possible to design an eyeglass lens that is matched to the wearer on the basis of that sensitivity.

(4) In the method for designing an eyeglass lens of the present embodiment, in the display of the image by the display device 50, a calibration image may be displayed for adjusting the positional relationship between the height of the eye of the subject and the position of the display image.

Due to this, it is possible to measure the sensitivity of the wearer in relation to the direction of his/her line of sight in a more accurate manner.

(5) In the method for designing an eyeglass lens of the present embodiment, in the evaluation of the sensitivity, the sensitivity of the subject to the direction of his/her line of sight at a short distance may be evaluated on the basis of the impressions received by the subject who has viewed the test images T, and the test images T may be at least one image selected from a portable telephone, a book, and a newspaper. Due to this, it is possible to employ an object which the subject sees on a daily basis at the near distance, so that this operation is better matched to an actual situation, and it is possible to measure the sensitivity of the wearer in relation to the direction of his/her line of sight in an accurate manner.

(6) In the method for designing an eyeglass lens of the present embodiment, in the evaluation of the sensitivity, the sensitivity of the subject to the direction of his/her line of sight at an intermediate distance may be evaluated on the basis of the impressions of the subject who has viewed the test images T, and the test images T may be at least one image selected from a personal computer, a tablet terminal, and a musical score. Due to this, it is possible to employ an object which the subject sees on a daily basis at the intermediate distance, so that this operation is better matched to an actual situation, and it is possible to measure the sensitivity of the wearer in relation to the direction of his/her line of sight in an accurate manner.

The following variations also come within the range of the present invention, and can also be combined with the embodiment described above.

Variation 1

In the embodiment described above, it was explained that the positions where the test images T were displayed were the positions P1 through P4 which were determined in advance. However, it would also be possible to capture an image of an object and of the subject who is viewing that object, to calculate relative positions of the object with respect to the left eye and the right eye of the subject from the captured image (hereinafter termed the "positional relationship image") by image processing, and to display images of the object at positions corresponding to those relative positions in the left eye image 501L and the right eye image 501R.

For example, the subject may be asked to operate a smartphone in an attitude that is the same as usual. And images of the eyes of the subject and the smartphone are captured while the subject is operating the smartphone. In order to obtain the relative positions of the eyes of the subject and the smartphone, it is desirable to capture images of the eyes of the subject and of the smartphone from a plurality of directions. From the positional relationship images that have thus been calculated, the positions of the eyes of the subject and the smartphone are calculated as three dimensional data, and an image of the smartphone is projected in the position where the display screen 501 is disposed, whereby it is possible to build up image data for the test images T.

In this manner, the designing method of this Variation includes capturing a positional relationship image that includes both the subject and the object, and, in the display of the test images T that are displayed upon the display device 50, images of the object are displayed as the test images T at positions that are set on the basis of the positional relationship between the subject and the object as obtained from the positional relationship image. Since, due to this, the attitude that the wearer adopts when looking at the object is captured, and the test images T are displayed upon the display device on the basis of the positional relationship image that has been captured, accordingly it is possible for the wearer to view images that may be supposed to be preferable for the wearer, and it is possible to measure the sensitivity of the wearer to the direction of his/her line of sight in a more accurate manner.

Variation 2

It would also be possible further to provide a line of sight direction detection function to the display device 50 of the embodiment described above, in which case the line of sight direction would be detected at the same time as line of sight direction sensitivity testing is performed.

Figure 28A:
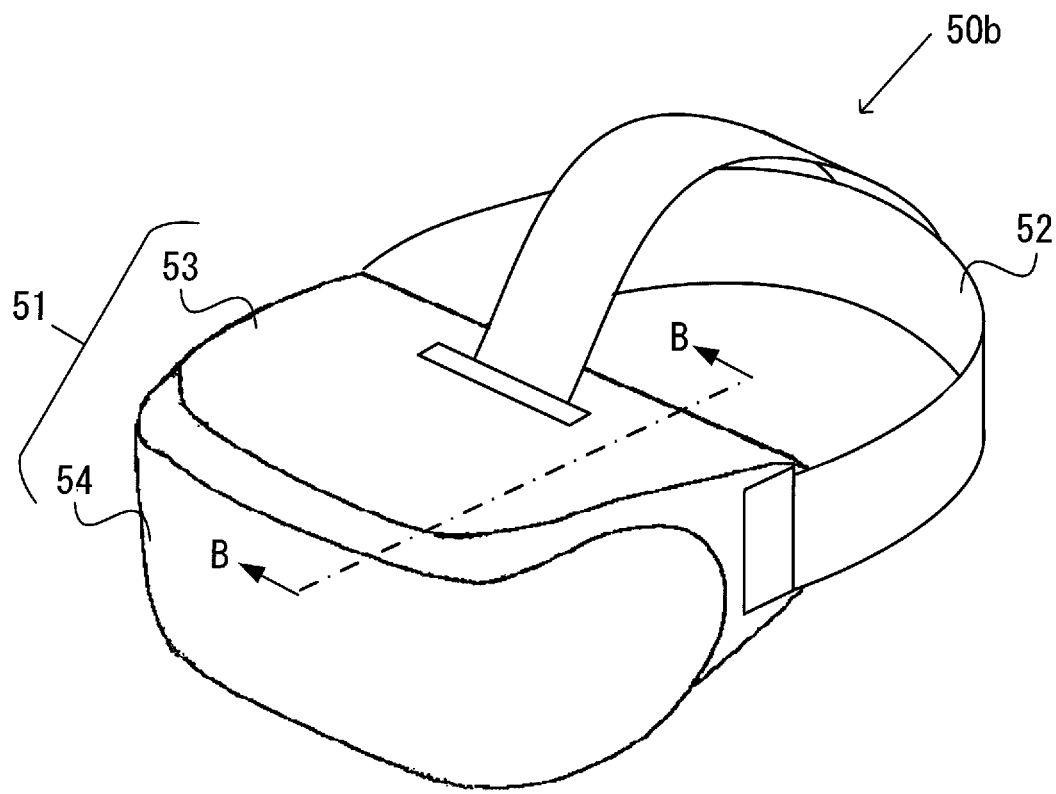
FIG. 28A is a perspective view showing external appearance of a display device related to a method for designing an eyeglass lens according to an embodiment.
Figure 28B:
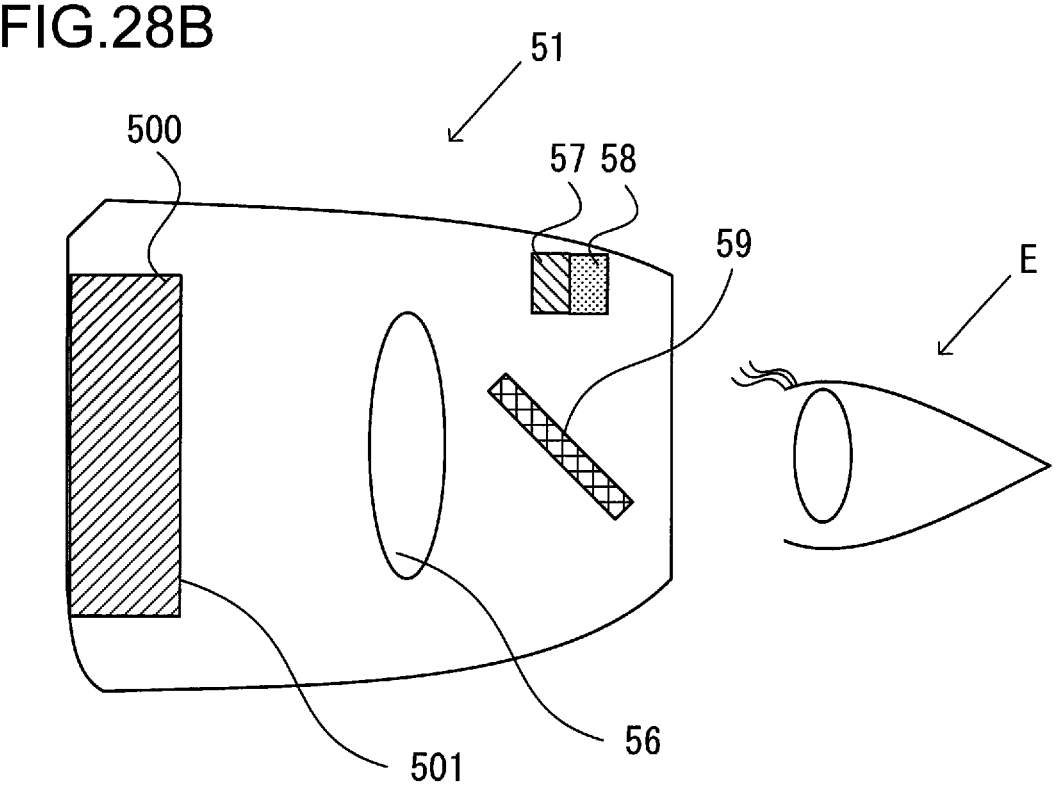
FIG. 28B is a perspective view showing an internal structure of a display device related to a method for designing an eyeglass lens according to an embodiment.

FIGS. 28A and 28B are figures showing a display device 50b that comprises a line of sight direction detector. FIG. 28A is a perspective view showing external appearance of this display device 50b. And FIG. 28B is a B-B sectional view, schematically showing an internal structure of the display device 50b. In addition to the configurations described above in connection with the previous embodiments, the main body 51 of the display device 50b also comprises an infrared emission unit 57, an image capturing unit 58, and a half mirror 59. The infrared emission unit 57, the image capturing unit 58, and the half mirror 59 constitute a line of sight direction detector.

The infrared emission unit 57 emits infrared rays. These infrared rays that are emitted are reflected by the half mirror 59 and illuminate the eye E of the subject, are reflected from a cornea or the like, are reflected by the half mirror 59 again, and then are received by the image capturing unit 58. From the captured image, the image capturing unit 58 may obtain the coordinate of the center of the pupil of the subject or the coordinate of the center of reflection of a cornea, and may calculate the direction of the line of sight of the subject on the basis of a correspondence formula between that coordinate and the direction of his/her line of sight, obtained in advance by calibration or the like. Since the half mirror 59 is transparent to visible light, accordingly it does not provide any hindrance when the subject is viewing the image upon the display screen 501.

In the line of sight direction sensitivity testing, when the wearer is viewing the test images T that are being displayed upon the display device 50b, by simultaneously detecting the direction of his/her line of sight, it is possible to acquire data specifying the tendency and so on of the direction of the line of sight of the wearer with respect to the object. The method for designing eyeglass lens of this variation includes detecting the direction of the line of sight of the subject who has viewed the display image, and, in the evaluation of the sensitivity, the sensitivity of the subject is evaluated on the basis of the line of sight direction. Due to this, it is possible to measure the sensitivity of the wearer to the direction of his/her line of sight with higher precision by also taking into account the data specifying his/her line of sight direction.

It should be understood that, with the method for designing an eyeglass lens of the embodiment described above, an example has been explained in which, principally, a target aberration distribution and/or a target power distribution for a progressive power lens is set, but the present invention is not limited to this application. It would also be possible to perform design related to a single focus lens by employing information related to the sensitivity of the wearer. In particular, in the design of a single focus lens, it is desirable to perform setting of the spherical power error, which is the deviation of the refractive power from the spherical power, and of the astigmatism, at the edge portions of the lens on the basis of the information related to the sensitivity of the wearer.

The present invention is not limited by the details of the embodiments described above. In particular, it would be possible to combine the items disclosed by the embodiments and variations described above in any appropriate combination. Moreover, other modes of realization that may be conceived within the range of the technical concept of the present invention are also included within the scope of the present invention.

REFERENCE SIGNS LIST

1: ordering device, 2: order receiving device, 10: eyeglass lens ordering and order receiving system, 11: control unit of ordering device, 13: communication unit of ordering device, 21: control unit of order receiving device, 23: communication unit of order receiving device, 50, 50a, 50b: display devices, 56: image formation lens, 100a, 100b, 100c: ordering screens, 106a, 106b, 106c: sensitivity information items, 500: portable terminal, 501: display screen, 501L: left eye image, 501R: right eye image, 511: display control unit, B, B1, B2, B3, B4, B5: blurred images, Bo, Yo: original images, C: intermediate area, F: distance area, La1, La2: side portions, N: near area, T: test image, U: non-side portion, Y, Y0a, Y0b, Y45a, Y45b, Y90a, Y90b, Y135a, Y135b: distorted images

The invention claimed is:

1. A method for designing an eyeglass lens, the method comprising:
  displaying an image upon a display device while maintaining a positional relationship of a face of a subject and the display device;
  acquiring information in which visual sensitivity of the subject is evaluated on the basis of an impression received by the subject who has viewed the image;
  designing an eyeglass lens at least partly on the basis of the information in which the sensitivity is evaluated;
  detecting movement of the subject, comprising movement detection; and
  changing the images on the basis of movement of the subject that has been detected, comprising image changing, wherein:
  in the display of the image, a plurality of images are displayed, each having different distortion;
  in the evaluation of the sensitivity, the sensitivity of the subject to distortion is evaluated on the basis of the impressions received by the subject who has viewed the plurality of images;
  parallax is present between a right eye image and a left eye image for enabling stereoscopic vision; and
  the images are processed images obtained by processing an image in which at least a portion of surroundings of the subject have been captured.

2. The method for designing an eyeglass lens according to claim 1, wherein:
  the display device is disposed at a position based upon a height of an eye of the subject.

3. The method for designing an eyeglass lens according to claim 1, wherein:
  the plurality of images differ by at least one of distortion level of the distortion and distortion direction of the distortion.

4. The method for designing an eyeglass lens according to claim 1, wherein:
  each of the images is distorted in at least one partial region.

5. The method for designing an eyeglass lens according to claim 4, wherein:
  the image is distorted both in one partial region on one side from the center of the image, and in a partial region on the side opposite to the one side from the center of the image.

6. The method for designing an eyeglass lens according to claim 1, wherein:
  the images are processed images obtained by processing an image depicting a virtual space.

7. The method for designing an eyeglass lens according to claim 1, further comprising:
  detecting a direction of a line of sight of the subject who has viewed the image, wherein:
  in the evaluation of the sensitivity, the sensitivity of the subject is further evaluated on the basis of the direction of the line of sight.

8. The method for designing an eyeglass lens according to claim 3, wherein:
  in the display of the image, a right eye image and a left eye image that are mutually different are displayed to the right eye and to the left eye of the subject, respectively.

9. The method for designing an eyeglass lens according to claim 8, wherein:
  the parallax between the right eye image and the left eye image is based on the mutually different right eye image and left eye image displayed to the right eye and the left eye of the subject, respectively.

10. A method for manufacturing an eyeglass lens, in which an eyeglass lens is manufactured that has been designed according to a method for designing an eyeglass lens according to claim 1.

11. An eyeglass lens, manufactured according to the method for manufacturing an eyeglass lens of claim 10.

12. The method for designing an eyeglass lens according to claim 1, wherein:
  each of the images is distorted in a plurality of partial regions.

13. The method for designing an eyeglass lens according to claim 12, wherein:
  in each of the plurality of partial regions, the images are mutually different with regard to at least one of the distortion level and the distortion direction.

14. The method for designing an eyeglass lens according to claim 1, wherein:
  each of the images is distorted in all regions.

15. A method for designing an eyeglass lens, the method comprising:
  displaying an image upon a display device while maintaining a positional relationship of a face of a subject and the display device;
  acquiring information in which visual sensitivity of the subject is evaluated on the basis of an impression received by the subject who has viewed the image;
  designing an eyeglass lens at least partly on the basis of the information in which the sensitivity is evaluated;
  detecting movement of the subject, comprising movement detection; and
  changing the images on the basis of movement of the subject that has been detected, comprising image changing, wherein:

in the display of the image, a plurality of images are displayed, each having a different range of blurring;

in the evaluation of the sensitivity, the sensitivity of the subject to blurring is evaluated on the basis of the impressions received by the subject who has viewed the plurality of images;

adjacent to the blurring, the images comprise a region in which the blurring level changes; and the images are processed images obtained by processing an image in which at least a portion of surroundings of the subject have been captured.

16. The method for designing an eyeglass lens according to claim 15, wherein:

in the plurality of images, blurring levels of the blurring and/or regions of the blurring are different.

17. The method for designing an eyeglass lens according to claim 15, wherein:

each of the images comprises a plurality of regions whose blurring levels are mutually different, and/or blurring in which the blurring level changes continuously.

18. The method for designing an eyeglass lens according to claim 8, wherein:

adjacent to the blurring, the images comprise the region, and in the region, the blurring level changes stepwise or continuously.

19. The method for designing an eyeglass lens according to claim 15, wherein:

in the display of the image, a region in which the blurring level is relatively large is displayed so as to be disposed below a region in which the blurring level is relatively small or a region where there is no blurring; and in the evaluation of the sensitivity, the sensitivity to blurring when the subject is looking at an object at a long distance is evaluated.

20. The method for designing an eyeglass lens according to claim 15, wherein:

in the display of the image, a region in which the blurring level is relatively large is displayed so as to be disposed above a region in which the blurring level is relatively small or a region where there is no blurring; and in the evaluation of the sensitivity, the sensitivity to blurring when the subject is looking at an object at a short distance is evaluated.

21. The method for designing an eyeglass lens according to claim 15, wherein:

in the display of the image, a region in which the blurring level is relatively small or a region where there is no blurring is displayed so as to be disposed surrounded by a region in which the blurring level is relatively large; and in the evaluation of the sensitivity, the sensitivity to blurring when the subject is looking at an object at an intermediate distance is evaluated.

22. A method for designing an eyeglass lens, the method comprising:

displaying an image upon a display device while maintaining a positional relationship of a face of a subject and the display device;

acquiring information in which visual sensitivity of the subject is evaluated on the basis of an impression received by the subject who has viewed the image; and designing an eyeglass lens at least partly on the basis of the information in which the sensitivity is evaluated;

detecting movement of the subject, comprising movement detection; and changing the images on the basis of movement of the subject that has been detected, comprising image changing, wherein:

in the display of the image, a plurality of images whose positions in a portion of a field of view of the subject are different are displayed while changing over between them;

in the evaluation of the sensitivity, the sensitivity of the subject to a direction of a line of sight at a predetermined distance is evaluated on the basis of the impressions received by the subject who has viewed the plurality of images;

in the display of the image, an image of an object is displayed as the image, and is displayed at a set position that is set on the basis of a positional relationship between the subject and the object; and the images are processed images obtained by processing an image in which at least a portion of surroundings of the subject have been captured.

23. The method for designing an eyeglass lens according to claim 22, wherein:

in the display of the image, a plurality of images are displayed at different heights; and the sensitivity of the subject to a height of a line of sight at the predetermined distance is evaluated on the basis of the impressions received by the subject who has viewed the plurality of images.

24. The method for designing an eyeglass lens according to claim 22, wherein:

the portion of the field of view corresponds to any one region selected from among a distance area of a progressive power lens, a near area thereof and an intermediate region thereof between the distant area and the near area; and the predetermined distance is a distance seen through the one region that has been selected.

25. The method for designing an eyeglass lens according to claim 22, wherein:

in the display of the image, a calibration image is displayed for adjusting a positional relationship between a height of an eye of the subject and a position of the image.

26. The method for designing an eyeglass lens according to claim 22, further comprising:

capturing a positional relationship image that includes the subject and an object, wherein:

in the display of the image, an image of an object is displayed as the image, and is displayed at a set position that is set on the basis of a positional relationship between the subject and the object, obtained from the positional relationship image.

27. The method for designing an eyeglass lens according to claim 22, wherein:

in the evaluation of the sensitivity, the sensitivity of the subject to a direction of a line of sight at a short distance is evaluated on the basis of the impressions received by the subject who has viewed the images; and the images are images of at least one selected from a portable telephone, a book, and a newspaper.

28. The method for designing an eyeglass lens according to claim 22, wherein:

in the evaluation of the sensitivity, the sensitivity of the subject to a direction of a line of sight at an intermediate distance is evaluated on the basis of the impressions received by the subject who has viewed the images; and the images are images of at least one selected from a personal computer, a tablet terminal, and a musical score.

29. An eyeglass lens ordering device, comprising:
an input unit that inputs information in which visual sensitivity of a subject is evaluated on the basis of an impression received by the subject who has viewed an image displayed while maintaining a positional relationship between a face of the subject and a display device, the positional relationship being maintained based on movement detection of the subject and a change of the image based on the movement detection,
in the display of the image, a plurality of images are displayed, each having different distortion, a different range of blurring, or a different position in a field of view; and
in the evaluation of the sensitivity, the sensitivity of the subject to distortion in which parallax is present between a right eye image and a left eye image for enabling stereoscopic vision, range of blurring wherein adjacent to the blurring the images comprise a region in which the blurring level changes, or position in a field of view in which in the display of the image, an image of an object is displayed as the image, and is displayed at a set position that is set on the basis of a positional relationship between the subject and the object is evaluated on the basis of the impressions received by the subject who has viewed the plurality of images;
the images are processed images obtained by processing an image in which at least a portion of surroundings of the subject have been captured; and
a communication unit that transmits the information inputted via the input unit, or a design parameter calculated on the basis of the information, to an eyeglass lens order receiving device.

30. An eyeglass lens ordering and order receiving and designing system, comprising:
the eyeglass lens ordering device according to claim 29; and
an eyeglass lens order receiving device comprising a reception unit that receives information relating to visual sensitivity of a subject, or a design parameter calculated on the basis of the information, the visual sensitivity being evaluated on the basis of an impression received by the subject who has viewed an image displayed while maintaining a positional relationship between a face of the subject and a display device and a design unit that designs an eyeglass lens at least partly on the basis of the information or the design parameter.

31. An eyeglass lens order receiving and designing device, comprising:
a reception unit that receives information relating to visual sensitivity of a subject, or a design parameter calculated on the basis of the information, the visual sensitivity being evaluated on the basis of an impression received by the subject who has viewed an image displayed while maintaining a positional relationship between a face of the subject and a display device, the positional relationship being maintained based on movement detection of the subject and a change of the image based on the movement detection,
in the display of the image, a plurality of images are displayed, each having a different distortion, a different range of blurring, or a different position in a field of view; and
in the evaluation of the sensitivity, the sensitivity of the subject to distortion in which parallax is present between a right eye image and a left eye image for enabling stereoscopic vision, range of blurring wherein adjacent to the blurring the images comprise a region in which the blurring level changes, or position in a field of view in which in the display of the image, an image of an object is displayed as the image, and is displayed at a set position that is set on the basis of a positional relationship between the subject and the object is evaluated on the basis of the impressions received by the subject who has viewed the plurality of images;
the images are processed images obtained by processing an image in which at least a portion of surroundings of the subject have been captured; and
a design unit that designs an eyeglass lens at least partly on the basis of the information or the design parameter.

* * * * *

UNITED STATES PATENT AND TRADEMARK OFFICE
CERTIFICATE OF CORRECTION

| | | |
|---|---|---|
| PATENT NO. | : 11,754,856 B2 | Page 1 of 1 |
| APPLICATION NO. | : 16/727242 | |
| DATED | : September 12, 2023 | |
| INVENTOR(S) | : Yoshinori Yoshida | |

It is certified that error appears in the above-identified patent and that said Letters Patent is hereby corrected as shown below:

In the Claims

Column 36, Line 24:
In Claim 8, delete "3," and insert --1,--.

Column 37, Line 23:
In Claim 18, delete "8," and insert --15,--.

Signed and Sealed this
Second Day of July, 2024

Katherine Kelly Vidal
*Director of the United States Patent and Trademark Office*